(12) United States Patent
Traina

(10) Patent No.: US 12,156,709 B2
(45) Date of Patent: Dec. 3, 2024

(54) HIGHLY ARTICULATED LAPAROSCOPIC JOINT INCLUDING ELECTRICAL SIGNAL TRANSMISSION THERETHROUGH

(71) Applicant: Covidien LP, Mansfield, MA (US)

(72) Inventor: Zachary Traina, Verona, NJ (US)

(73) Assignee: Covidien LP, Mansfield, MA (US)

( * ) Notice: Subject to any disclaimer, the term of this patent is extended or adjusted under 35 U.S.C. 154(b) by 724 days.

(21) Appl. No.: 17/276,511

(22) PCT Filed: Sep. 10, 2019

(86) PCT No.: PCT/US2019/050272
§ 371 (c)(1),
(2) Date: Mar. 16, 2021

(87) PCT Pub. No.: WO2020/060792
PCT Pub. Date: Mar. 26, 2020

(65) Prior Publication Data
US 2021/0290322 A1 Sep. 23, 2021

(51) Int. Cl.
*A61B 34/30* (2016.01)
*A61B 17/00* (2006.01)
(Continued)

(52) U.S. Cl.
CPC ........ *A61B 34/30* (2016.02); *A61B 17/07207* (2013.01); *A61B 18/14* (2013.01);
(Continued)

(58) Field of Classification Search
CPC ... A61B 34/30; A61B 17/07207; A61B 18/14; A61B 34/71; A61B 2017/00022;
(Continued)

(56) References Cited

U.S. PATENT DOCUMENTS

| 5,710,870 A | 1/1998 | Ohm et al. |
| 5,797,900 A | 8/1998 | Madhani et al. |

(Continued)

FOREIGN PATENT DOCUMENTS

| CN | 109937013 A | * | 6/2019 | ............ A61B 17/29 |
| EP | 2659854 A2 | | 11/2013 | |

(Continued)

OTHER PUBLICATIONS

Extended European Search Report issued in corresponding application EP 19863144.2 dated Sep. 6, 2022 (12 pages).

(Continued)

*Primary Examiner* — Joseph M Dietrich
*Assistant Examiner* — Michael T. Holtzclaw
(74) *Attorney, Agent, or Firm* — Carter, DeLuca & Farrell LLP

(57) ABSTRACT

A robotic electromechanical surgical instrument includes a housing, an elongated shaft that extends distally from the housing, a wrist assembly supported on the elongated shaft, an end effector coupled to the wrist assembly, cables coupled to the wrist assembly, and an electrical cable coupled to the end effector. The wrist assembly includes a first joint coupled to a second joint. The first joint includes a proximal segment defining an arcuate surface and a distal segment defining an arcuate surface. The electrical cable is positioned relative to the proximal arcuate surface and the distal arcuate surface such that during articulation of the wrist assembly the electrical cable rolls off of the distal arcuate surface as the electrical cable rolls on to the proximal arcuate surface and the electrical cable rolls off of the proximal arcuate surface as the electrical cable rolls on to the distal arcuate surface.

20 Claims, 18 Drawing Sheets

(51) Int. Cl.
    *A61B 17/072*     (2006.01)
    *A61B 18/14*      (2006.01)
    *A61B 34/00*      (2016.01)
    *A61B 17/29*      (2006.01)

(52) U.S. Cl.
    CPC .... *A61B 34/71* (2016.02); *A61B 2017/00022* (2013.01); *A61B 2017/00327* (2013.01); *A61B 2017/07257* (2013.01); *A61B 2017/07271* (2013.01); *A61B 2017/2927* (2013.01); *A61B 2034/305* (2016.02)

(58) Field of Classification Search
    CPC  A61B 2017/07257; A61B 2017/07271; A61B 2034/305
    USPC .......................................................... 606/1
    See application file for complete search history.

(56) References Cited

U.S. PATENT DOCUMENTS

| | | | | |
|---|---|---|---|---|
| 8,523,900 | B2* | 9/2013 | Jinno | A61B 34/37 |
| | | | | 606/208 |
| 11,109,925 | B2* | 9/2021 | Cooper | A61B 17/00234 |
| 2004/0199147 | A1 | 10/2004 | Nishizawa et al. | |
| 2005/0040664 | A1 | 2/2005 | Kameda et al. | |
| 2008/0119870 | A1* | 5/2008 | Williams | A61B 34/71 |
| | | | | 606/130 |
| 2010/0016852 | A1 | 1/2010 | Manzo et al. | |
| 2016/0166347 | A1 | 6/2016 | Kishi | |
| 2017/0252096 | A1 | 9/2017 | Felder et al. | |
| 2018/0206904 | A1 | 7/2018 | Felder et al. | |
| 2018/0304389 | A1* | 10/2018 | Simi | A61B 17/00 |
| 2019/0117247 | A1* | 4/2019 | Kim | A61B 34/74 |
| 2019/0328467 | A1* | 10/2019 | Waterbury | A61B 34/30 |
| 2021/0169597 | A1* | 6/2021 | Abbott | A61B 34/35 |

FOREIGN PATENT DOCUMENTS

| | | | |
|---|---|---|---|
| EP | 2240095 B1 | 9/2015 | |
| JP | 2009136684 A | 6/2009 | |
| JP | 2011072574 A | 4/2011 | |
| JP | 2014513570 A | 6/2014 | |
| WO | 2016148463 A1 | 9/2016 | |
| WO | WO-2018049211 A1 * | 3/2018 | ....... A61B 17/00234 |

OTHER PUBLICATIONS

International Search Report and Written Opinion of the International Searching Authority issued in corresponding Int'l Appl. No. PCT/US2019/050272 dated Dec. 27, 2019 (12 pages).
Office Action issued in corresponding Japanese Appliation No. 2021-514564 mailed May 19, 2022, together with English language translation (10 pages).
Canadian Office Action dated Jan. 21, 2023, issued in corresponding Canadian Appln. No. 3,110,703, 5 pages.
Extended European Search Report issued in European Patent Application No. 23163383.5 dated Jul. 5, 2023 (10 pages).
Examination Report No. 1 issued in corresponding Australian Appl. No. 2019344528 dated Aug. 12, 2021 (3 pages).

* cited by examiner

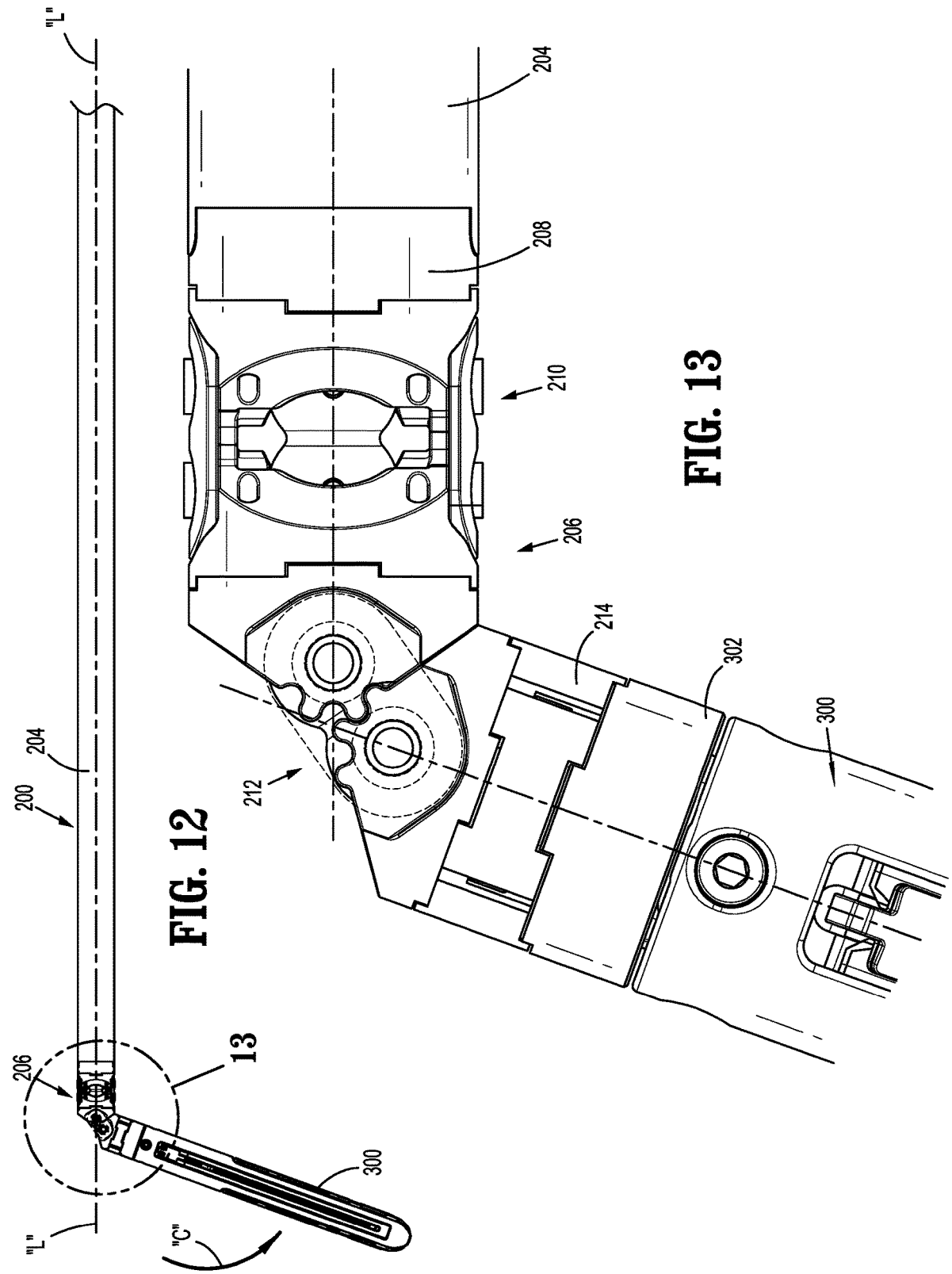

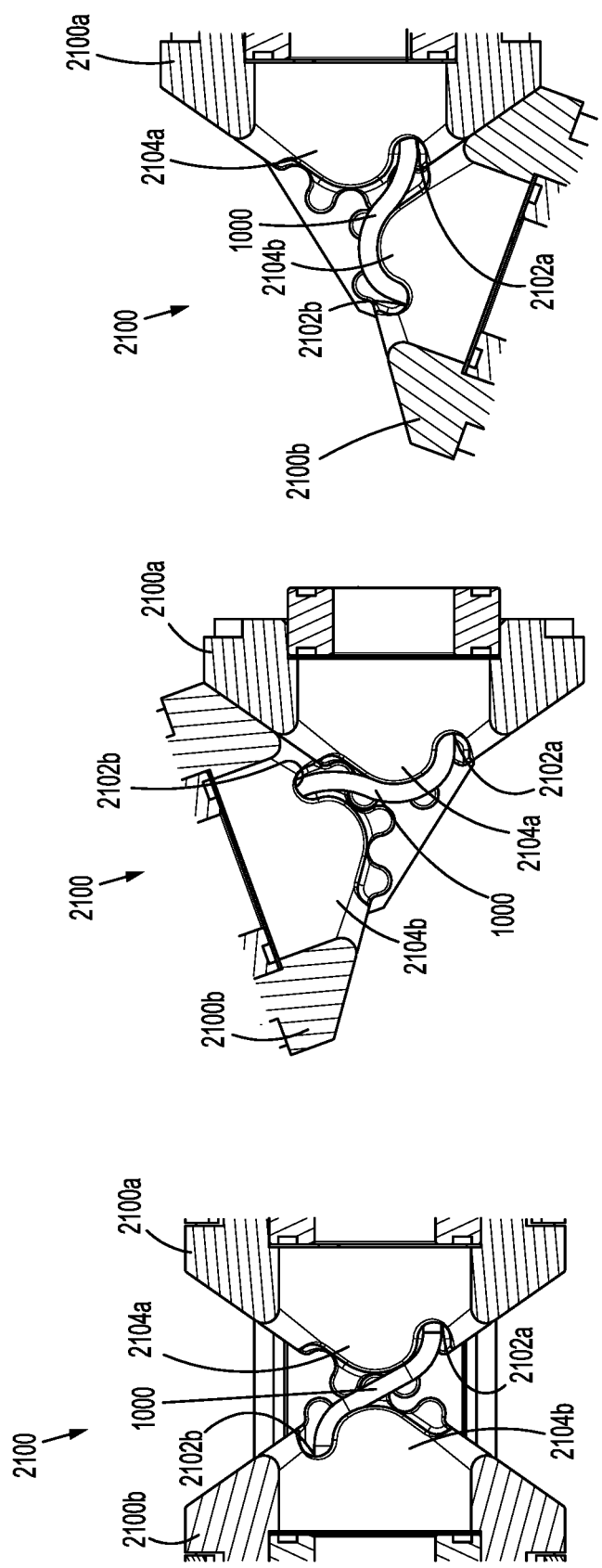

HIGHLY ARTICULATED LAPAROSCOPIC JOINT INCLUDING ELECTRICAL SIGNAL TRANSMISSION THERETHROUGH

CROSS-REFERENCE TO RELATED APPLICATION

The present application is a U.S. National Stage Application filed under 35 U.S.C. § 371(a) of International Patent Application Serial No. PCT/US2019/050272, filed Sep. 10, 2019, which claims the benefit of and priority to U.S. Provisional Patent Application Ser. No. 62/732,108, filed Sep. 17, 2018, the entire disclosure of which is incorporated by reference herein.

International Patent Application Serial No. PCT/US2019/050272 is also a Continuation-in-Part Application of International Patent Application Serial No. PCT/US2019/012017, filed Jan. 2, 2019 (now U.S. patent application Ser. No. 16/769,938, filed under 35 U.S.C. § 371(a) on Jun. 4, 2020) which claims the benefit of and priority to U.S. Provisional Application Ser. No. 62/613,567, filed on Jan. 4, 2018, the entire content of which is incorporated herein by reference.

BACKGROUND

Robotic surgical systems have been used in minimally invasive medical procedures. Some robotic surgical systems include a console supporting a surgical robotic arm and a surgical instrument having at least one end effector (e.g., a forceps or a stapling device) mounted to the robotic arm. The robotic arm provides mechanical power to the surgical instrument for its operation and movement. Each robotic arm may include an instrument drive unit that is operatively connected to the surgical instrument. The surgical instruments may include cables that are motor driven to operate end effectors of the surgical instruments.

SUMMARY

The present disclosure relates to surgical instruments for use in surgical procedures. More specifically, the present disclosure relates to articulable robotic surgical instruments for robotic surgical systems used to conduct minimally invasive surgical procedures. The present disclosure provides for small surgical instruments for robotic surgical systems that provide increased articulation, torque transmission, and mechanical manipulation.

In accordance with an aspect of the present disclosure, a robotic electromechanical surgical instrument is provided. The surgical instrument includes a housing, an elongated shaft that extends distally from the housing, a wrist assembly supported on the elongated shaft, an end effector coupled to the wrist assembly, cables coupled to the wrist assembly, and an electrical cable coupled to the end effector.

The elongated shaft defines a longitudinal axis. The wrist assembly includes a first joint coupled to a second joint. The cables are movable to manipulate the first and second joints to enable the wrist assembly to articulate relative to the longitudinal axis. The first joint includes a proximal segment defining an arcuate surface and a distal segment defining an arcuate surface. The electrical cable is positioned relative to the proximal arcuate surface and the distal arcuate surface such that, during articulation of the wrist assembly, the electrical cable rolls off of the distal arcuate surface as the electrical cable rolls on to the proximal arcuate surface, and the electrical cable rolls off of the proximal arcuate surface as the electrical cable rolls on to the distal arcuate surface.

The proximal and distal segments of the first joint are supported for movement relative to one another to facilitate articulation of the wrist assembly relative to the longitudinal axis of the elongated shaft. A link may be coupling the proximal segment of the first joint to the distal segment of the first joint.

In certain aspects, the proximal segment of the first joint defines a proximal aperture and the distal segment of the first joint defines a distal aperture which is misaligned with the proximal aperture. The electrical cable may be disposed through the proximal aperture and the distal aperture.

In certain aspects, the electrical cable is positioned between the proximal segment and the distal segment of the first joint such that, as the distal segment articulates relative to the proximal segment, the electrical wire rolls onto the distal arcuate surface at a rate and the electrical wire rolls off of the proximal arcuate surface at the same rate.

In some aspects, the electrical cable is configured to transmit electrosurgical treatment energy to a portion of the end effector. Additionally, or alternatively, the electrical cable is configured to transmit a sensor signal from the end effector.

In some aspects, the second joint includes a proximal segment defining a proximal arcuate surface and a distal segment defining a distal arcuate surface. The electrical cable may be positioned relative to the proximal arcuate surface of the second joint and the distal arcuate surface of the second joint such that, during articulation of the wrist assembly, the electrical cable rolls off of the distal arcuate surface of the second joint as the electrical cable rolls on to the proximal arcuate surface of the second joint, and the electrical cable rolls off of the proximal arcuate surface of the second joint as the electrical cable rolls on to the distal arcuate surface of the second joint.

In certain aspects, the electromechanical surgical instrument may include a second electrical cable. The proximal segment of the first joint may define a second proximal arcuate surface, the distal segment of the first joint may define a second distal arcuate surface, and the second electrical cable is positioned such that, during articulation of the wrist assembly, the second electrical cable rolls off of the second distal arcuate surface as the electrical cable rolls on to the second proximal arcuate surface, and the second electrical cable rolls off of the second proximal arcuate surface as the second electrical cable rolls on to the second distal arcuate surface.

In certain aspects, the housing includes an electrical contact disposed thereon and the electrical cable is coupled to the electrical contact.

According to another aspect, a wrist assembly for use with an electromechanical surgical instrument is provided. The wrist assembly includes a first joint and a second joint operably coupled to the first joint and a plurality of cables coupled to at least one of the first joint or the second joint. The plurality of cables are movable to manipulate the first and second joints to enable the wrist assembly to articulate relative to a longitudinal axis defined by the wrist assembly in an unarticulated position. The first joint includes a proximal segment defining a proximal arcuate surface and a distal segment defining a distal arcuate surface. An electrical cable is positioned relative to the proximal arcuate surface and the distal arcuate surface such that, during articulation of the wrist assembly, the electrical cable rolls off of the distal arcuate surface as the electrical cable rolls on to the proximal arcuate surface, and the electrical cable rolls off of the proximal arcuate surface as the electrical cable rolls on to the distal arcuate surface.

In certain aspects, the proximal segment of the first joint defines a proximal aperture and the distal segment of the first joint defines a distal aperture which is misaligned with the proximal aperture. The electrical cable may be disposed through the proximal aperture and the distal aperture. A link may be coupling the proximal segment of the first joint to the distal segment of the first joint.

In certain aspects, the electrical cable is positioned between the proximal segment and the distal segment of the first joint such that, as the distal segment articulates relative to the proximal segment, the electrical wire rolls onto the distal arcuate surface at a rate and the electrical wire rolls off of the proximal arcuate surface at the same rate.

In some aspects, the electrical cable is configured to transmit electrosurgical treatment energy to a portion of the end effector. Additionally, or alternatively, the electrical cable is configured to transmit a sensor signal from the end effector.

In some aspects, the second joint includes a proximal segment defining a proximal arcuate surface and a distal segment defining a distal arcuate surface. The electrical cable may be positioned relative to the proximal arcuate surface of the second joint and the distal arcuate surface of the second joint such that, during articulation of the wrist assembly, the electrical cable rolls off of the distal arcuate surface of the second joint as the electrical cable rolls on to the proximal arcuate surface of the second joint, and the electrical cable rolls off of the proximal arcuate surface of the second joint as the electrical cable rolls on to the distal arcuate surface of the second joint.

In certain aspects, the wrist assembly may include a second electrical cable. The proximal segment of the first joint may define a second proximal arcuate surface, the distal segment of the first joint may define a second distal arcuate surface, and the second electrical cable is positioned such that, during articulation of the wrist assembly, the second electrical cable rolls off of the second distal arcuate surface as the electrical cable rolls on to the second proximal arcuate surface, and the second electrical cable rolls off of the second proximal arcuate surface as the second electrical cable rolls on to the second distal arcuate surface.

Advantageously, the presently disclosed surgical instruments provide deterministic end effector position while resisting external loading (e.g., from the patient anatomy) from affecting the drive system. In addition, the presently disclosed surgical instruments include knuckle gearing (or coupling) with interlocking geometry that maintains rolling contact between gears to prevent 'S' condition in the joint where the end effector location would be non-deterministic.

The presently disclosed surgical instruments also provide high articulation (e.g., +/−70 degrees) in two directions while maintaining minimal bend radius. In some embodiments, additional cables can be routed to provide additional mechanical functionality at the end effector (e.g., a dedicated grasp function).

Additionally, the presently disclosed surgical instruments and wrist assemblies include structural features that facilitate passage of electrical cables therethrough with minimal resistance and minimal stress imparted on electrical cables during articulation of wrist assembly. Despite high articulation of the components of wrist assembly, the electrical cables do not translate longitudinally through any of the joints or components of the wrist assembly. This eliminates the need for tensioning or payout mechanisms that would otherwise be required to drive any cables or wires during articulation. Elimination of longitudinal translation of electrical cables also reduces the possibility of failures due to wear and abrasion of electrical cables and any components in contact with electrical cables. The electrical cables bend through only a single axis during articulation of the wrist assembly, as opposed to being bend in multiple directions, which significantly extends the lifetime of the electrical cables and even the components the electrical cables are in contact with. Additionally, the electrical cables are positioned within the wrist assembly, beneath drive cabling and shielding structures throughout the full articulation range, which reduces chances of damage to the electrical wires from incidental contact and reprocessing.

Other aspects, features, and advantages provided by some or all of the illustrative embodiments described herein will be apparent from the description, the drawings, and the claims that follow.

BRIEF DESCRIPTION OF THE DRAWINGS

The accompanying drawings, which are incorporated in and constitute a part of this specification, illustrate embodiments of the present surgical instruments for robotic surgical systems and, together with a general description of the disclosure given above, and the detailed description of the embodiment(s) given below, serve to explain the principles of the disclosure, wherein:

FIG. 12 is a top view of a distal portion of the surgical instrument of FIG. 2 with the wrist assembly thereof shown in an articulated position;

FIG. 13 is an enlarged view of the indicated area of detail shown in FIG. 12;

FIG. 19A is a cross-sectional view of a first joint of the wrist assembly of FIG. 18 in an unarticulated position;

FIG. 19B is a cross-sectional view of the first joint of the wrist assembly of FIG. 18 in an articulated position;

FIG. 19C is a cross-sectional view of the first joint of the wrist assembly of FIG. 18 in another articulated position;

DETAILED DESCRIPTION

Figure 1:
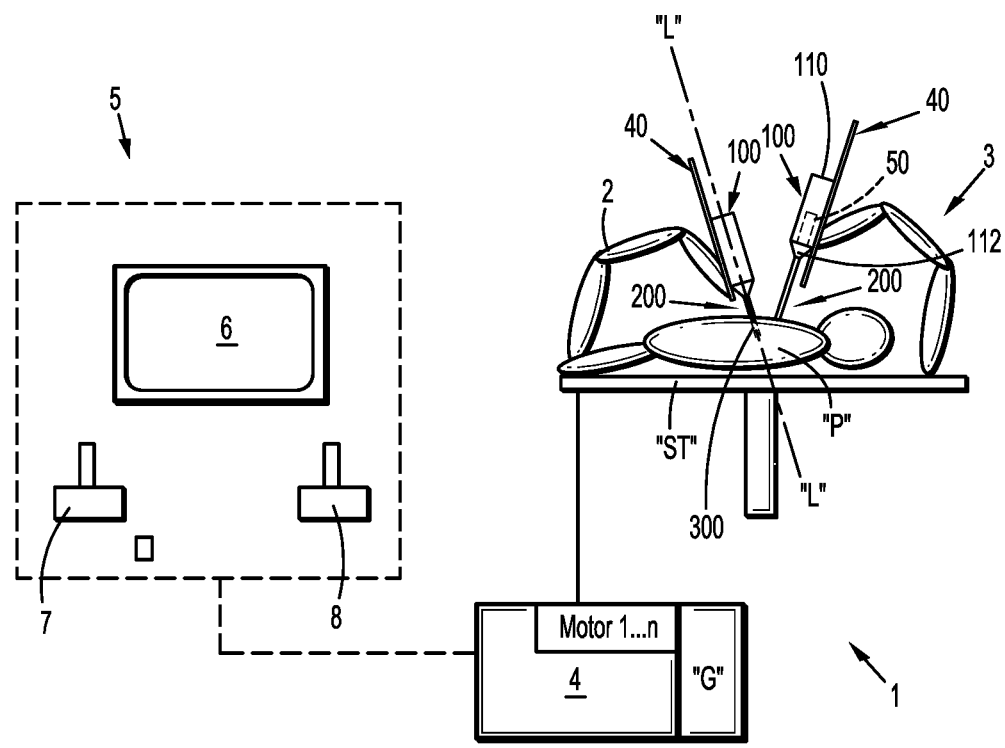
FIG. 1 is a schematic illustration of a robotic surgical system in accordance with the present disclosure.

Embodiments of the present surgical instruments for robotic surgical systems are described in detail with reference to the drawings, in which like reference numerals designate identical or corresponding elements in each of the several views. As used herein, the term "distal" refers to structure that is closer to a patient, while the term "proximal" refers to structure farther from the patient.

As used herein, the term "clinician" refers to a doctor, nurse, or other care provider and may include support personnel. In the following description, well-known functions or constructions are not described in detail to avoid obscuring the present disclosure in unnecessary detail.

Referring initially to FIG. 1, a surgical system, such as, for example, a robotic surgical system 1, generally includes one or more surgical robotic arms 2, 3, a control device 4, and an operating console 5 coupled with control device 4. Any of the surgical robotic arms 2, 3 may have a robotic surgical assembly 100 and an electromechanical surgical instrument 200 coupled thereto. Electromechanical surgical instrument 200 includes an end effector 300 disposed at a distal portion thereof. In some embodiments, robotic surgical assembly 100 may be removably attached to a slide rail 40 of one or more of surgical robotic arms 2, 3. In certain embodiments, robotic surgical assembly 100 may be fixedly attached to slide rail 40 of one or more of surgical robotic arms 2, 3.

Operating console 5 of robotic surgical system 1 includes a display device 6, which is set up to display three-dimensional images; and manual input devices 7, 8, by means of which a clinician (not shown), is able to telemanipulate the robotic arms 2, 3 of robotic surgical system 1 in a first operating mode, as known in principle to a person skilled in the art. Each robotic arm of robotic arms 2, 3 may be composed of any number of members, which may be connected through any number of joints. Robotic arms 2, 3 may be driven by electric drives (not shown) that are connected to control device 4. Control device 4 (e.g., a computer) of robotic surgical system 1 is set up to activate the drives, for example, by means of a computer program, in such a way that robotic arms 2, 3, the attached robotic surgical assembly 100, and thus electromechanical surgical instrument 200 (including end effector 300) of robotic surgical system 1 execute a desired movement according to a movement defined by means of manual input devices 7, 8. Control device 4 may be set up in such a way that it regulates movement of robotic arms 2, 3 and/or of the drives.

Robotic surgical system 1 is configured for use on a patient "P" positioned (e.g., lying) on a surgical table "ST" to be treated in a minimally invasive manner by means of a surgical instrument, e.g., electromechanical surgical instrument 200 and, more specifically, end effector 300 of electromechanical surgical instrument 200. Robotic surgical system 1 may include more than two robotic arms 2, 3, the additional robotic arms are likewise connected to control device 4 and telemanipulatable by means of operating console 5. A surgical instrument, for example, electromechanical surgical instrument 200 (including end effector 300 thereof), may also be attached to any additional robotic arm(s).

Control device 4 of robotic surgical system 1 may control one or more motors (not shown), each motor configured to drive movement of robotic arms 2, 3 in any number of directions. Control device 4 may control an instrument drive unit 110 including one or more motors 50 (or motor packs). Motors 50 drive various operations of end effector 300 of electromechanical surgical instrument 200. Motors 50 may include a rotation motor, such as, for example, a canister motor. One or more of motors 50 (or a different motor, not shown) may be configured to drive a rotation of electromechanical surgical instrument 200, or components thereof, relative to a longitudinal axis "L-L" thereof. The one or more motors can be configured to effect operation and/or movement of electromechanical end effector 300 of electromechanical surgical instrument 200.

Figure 2:
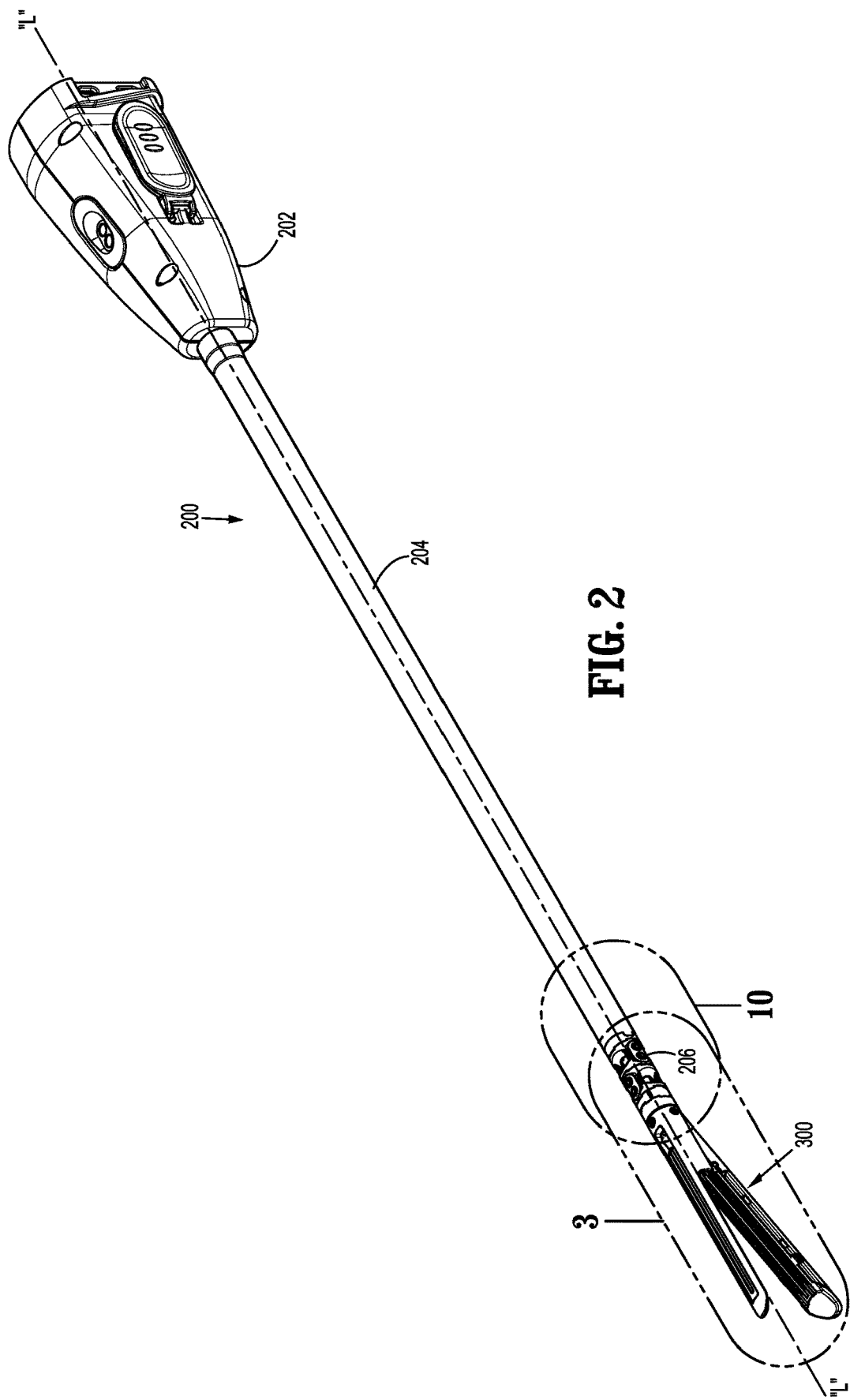
FIG. 2 is a perspective view of a surgical instrument of the robotic surgical system of FIG. 1 in an unarticulated position.

Turning now to FIG. 2, electromechanical surgical instrument 200 of robotic surgical system 1 includes a housing 202 at a proximal end portion thereof and an elongated shaft 204 that extends distally from housing 202. Elongated shaft 204 includes a wrist assembly 206 supported on a distal end portion of elongated shaft 204 that couples end effector 300 to elongated shaft 204.

Housing 202 of electromechanical surgical instrument 200 is configured to selectively couple to instrument drive unit 110 of robotic surgical assembly 100, for example, via side loading on a sterile interface module 112 of robotic surgical assembly 100, to enable motors 50 of instrument drive unit 110 of robotic surgical assembly 100 to operate end effector 300 of electromechanical surgical instrument 200. Housing 202 of electromechanical surgical instrument 200 supports a drive assembly 203 that mechanically and/or electrically cooperates with motors 50 of instrument drive unit 110 of robotic surgical assembly 100.

Figure 3:
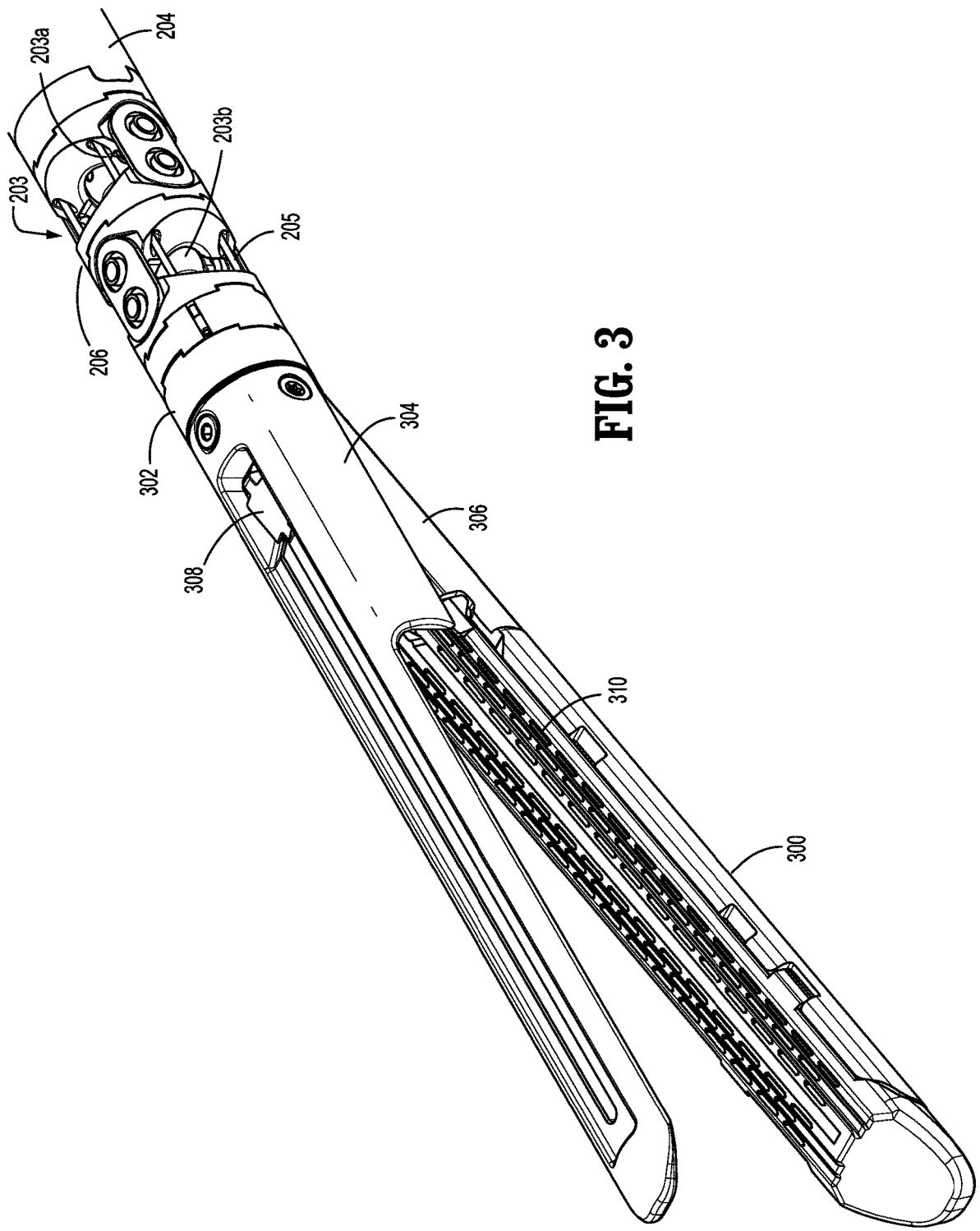
FIG. 3 is an enlarged, perspective view of the indicated area of detail shown in FIG. 2.
Figure 4:
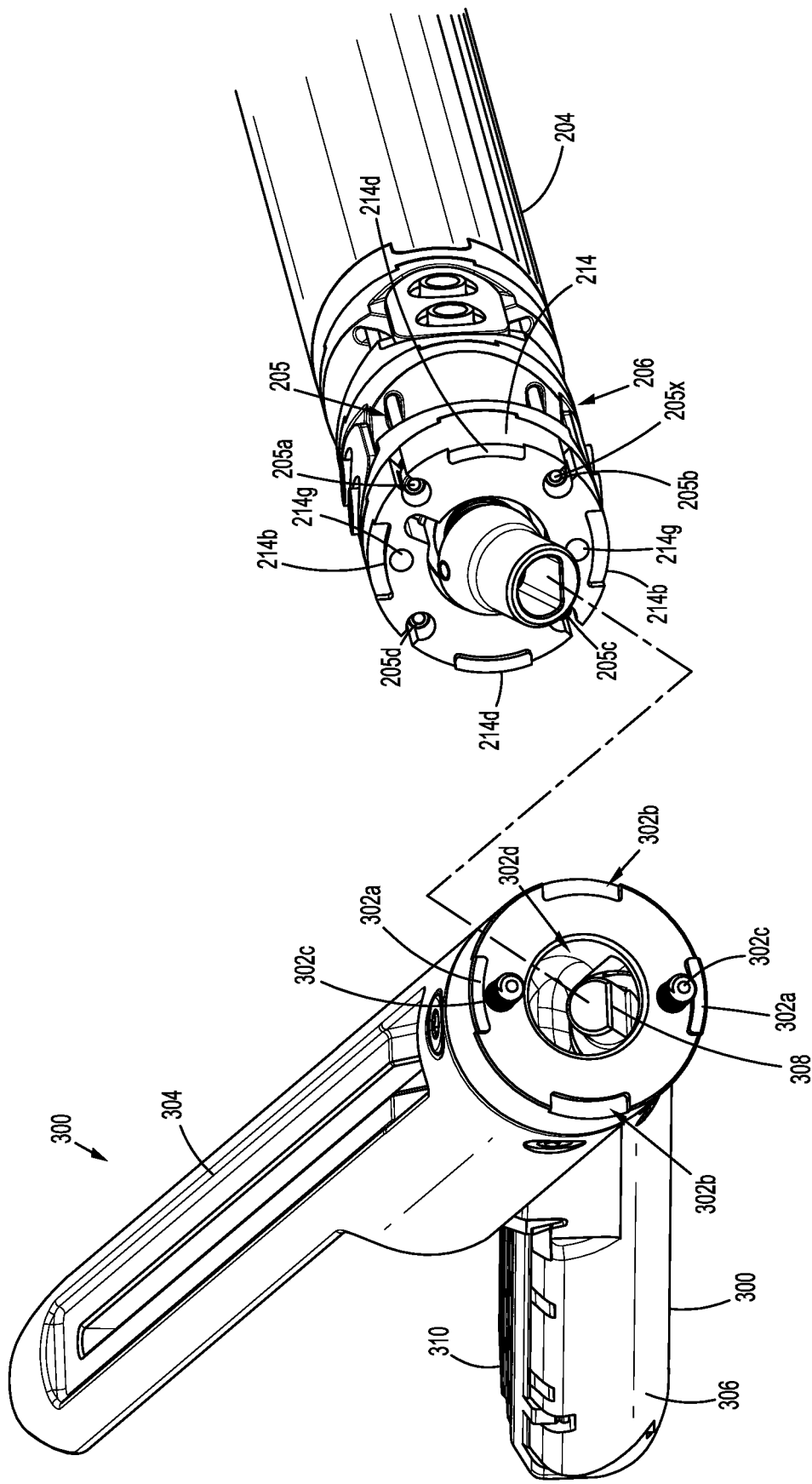
FIG. 4 is a perspective view of an end effector of the surgical instrument of FIG. 2 shown separated from a wrist assembly of an elongated shaft assembly of the surgical instrument.

Drive assembly 203 of electromechanical surgical instrument 200 can include any suitable electrical and/or mechanical component to effectuate driving force/movement, and which components may be similar to components of the drive assembly described in commonly owned International Application Publication No. WO2017053358, filed Sep. 21, 2016, the entire disclosure of which is incorporated by reference herein. In particular, as seen in FIGS. 3 and 4, drive assembly 203 of electromechanical surgical instrument 200 includes a cable drive assembly 203a and a firing assembly 203b. The cable drive assembly 203a is similar to that described in commonly owned U.S. Patent Application Publication No. 2015/0297199, filed Oct. 22, 2015 and entitled "Adapter Assembly with Gimbal for Interconnecting Electromechanical Surgical Devices and Surgical Loading Units, and Surgical Systems Thereof," the entire disclosure of which is incorporated by reference herein.

Figure 15:
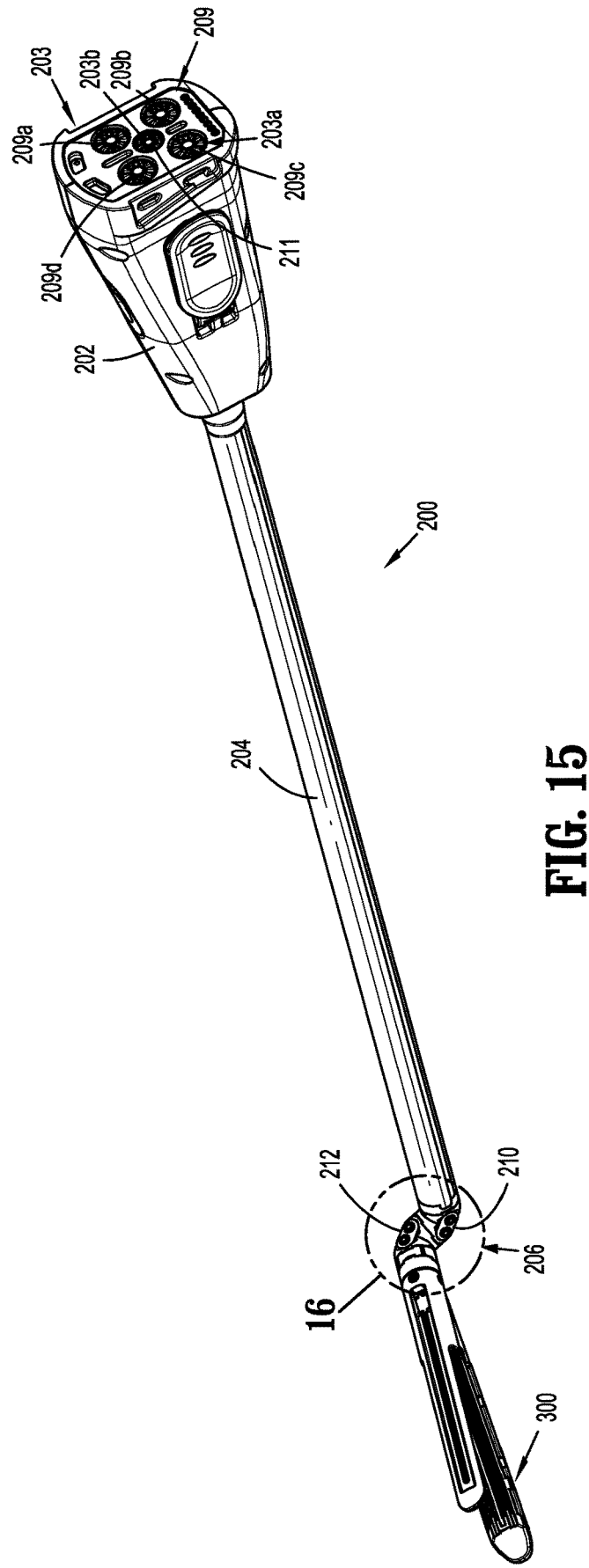
FIG. 15 is a perspective view of the surgical instrument of FIG. 2 shown in an exemplary articulated position.

With reference to FIGS. 1 and 15, cable drive assembly 203a of electromechanical surgical instrument 200 includes one or more driven members 209, such as driven members 209a, 209b, 209c, 209d (FIG. 15), to enable robotic surgical assembly 100 to transfer power and actuation forces from motors 50 of robotic surgical assembly 100 to ultimately drive movement of components of end effector 300 of electromechanical surgical instrument 200.

As seen in FIGS. 3 and 4, cable drive assembly 203a of electromechanical surgical instrument 200 includes cables 205, such as cables 205a, 205b, 205c, and 205d, which are coupled to a respective driven member 209a, 209b, 209c, 209d (FIG. 15) of electromechanical surgical instrument 200 at a proximal end portion thereof. Cables 205 of cable drive assembly 203a extend distally to distal end portions thereof, and may include ferrules 205x (FIG. 4) that couple to wrist assembly 206 of elongated shaft 204 at circumferentially spaced apart locations (e.g., angularly displaced) about the longitudinal axis "L-L" to enable cables 205 to effectuate an articulation/pitch/yaw of wrist assembly 206 of electromechanical surgical instrument 200 and end effector 300 of electromechanical surgical instrument 200 upon actuation of one or more of cables 205. Cable drive assembly 203a can include one or more pulleys, friction wheels, gears, couplers, rack and pinion arrangements, etc. coupled directly or indirectly to driven members 209 and/or cables 205 to facilitate driving movement imparted through driven members 209 and/or cables 205. The cables 205 can be arranged such that diagonal cables (e.g. cables 205d, 205b or cables 205a, 205c; see FIG. 4) can be positioned to be driven in opposite directions in order to provide articulation in multiple axes (e.g. two). Although only four cables are shown, cable drive assembly 203a can include any number of cables, for example, to provide additional functionally at the end effector 300.

Figure 5:
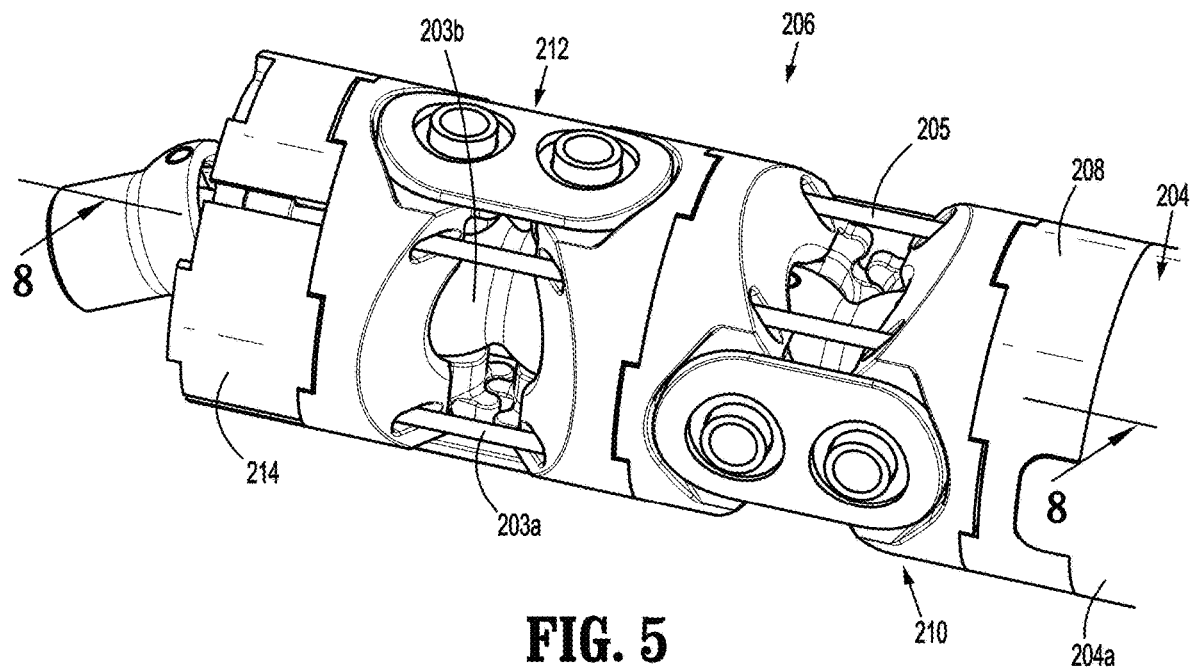
FIGS. 5 and 6 are perspective views of the wrist assembly of FIG. 4.
Figure 6:
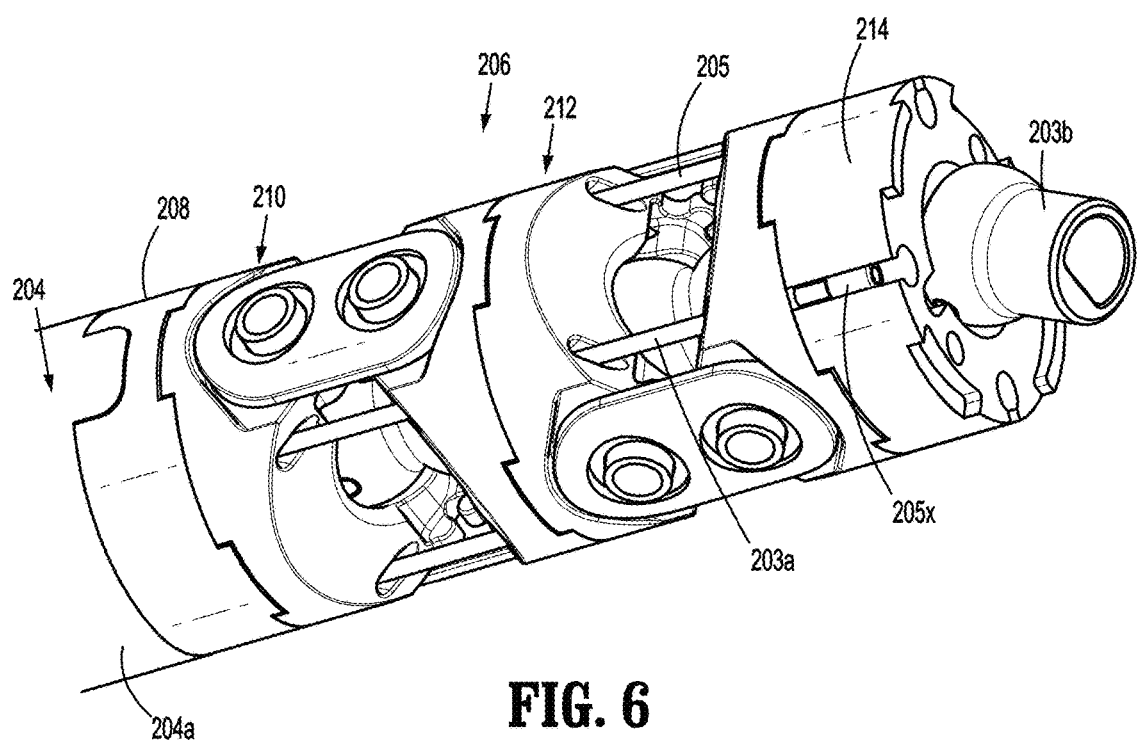

Turning to FIGS. 5 and 6, wrist assembly 206 of elongated shaft 204 of electromechanical surgical instrument 200 includes, from proximal to distal, a first interface 208 coupled to a distal portion of an outer tube 204a of elongated shaft 204, a first joint 210 coupled to a distal portion of first interface 208, a second joint 212 coupled to a distal portion of first joint 210 and angularly displaced therefrom (e.g., offset 90 degrees), and a second interface 214 coupled to a distal portion of second joint 212.

Figure 7:
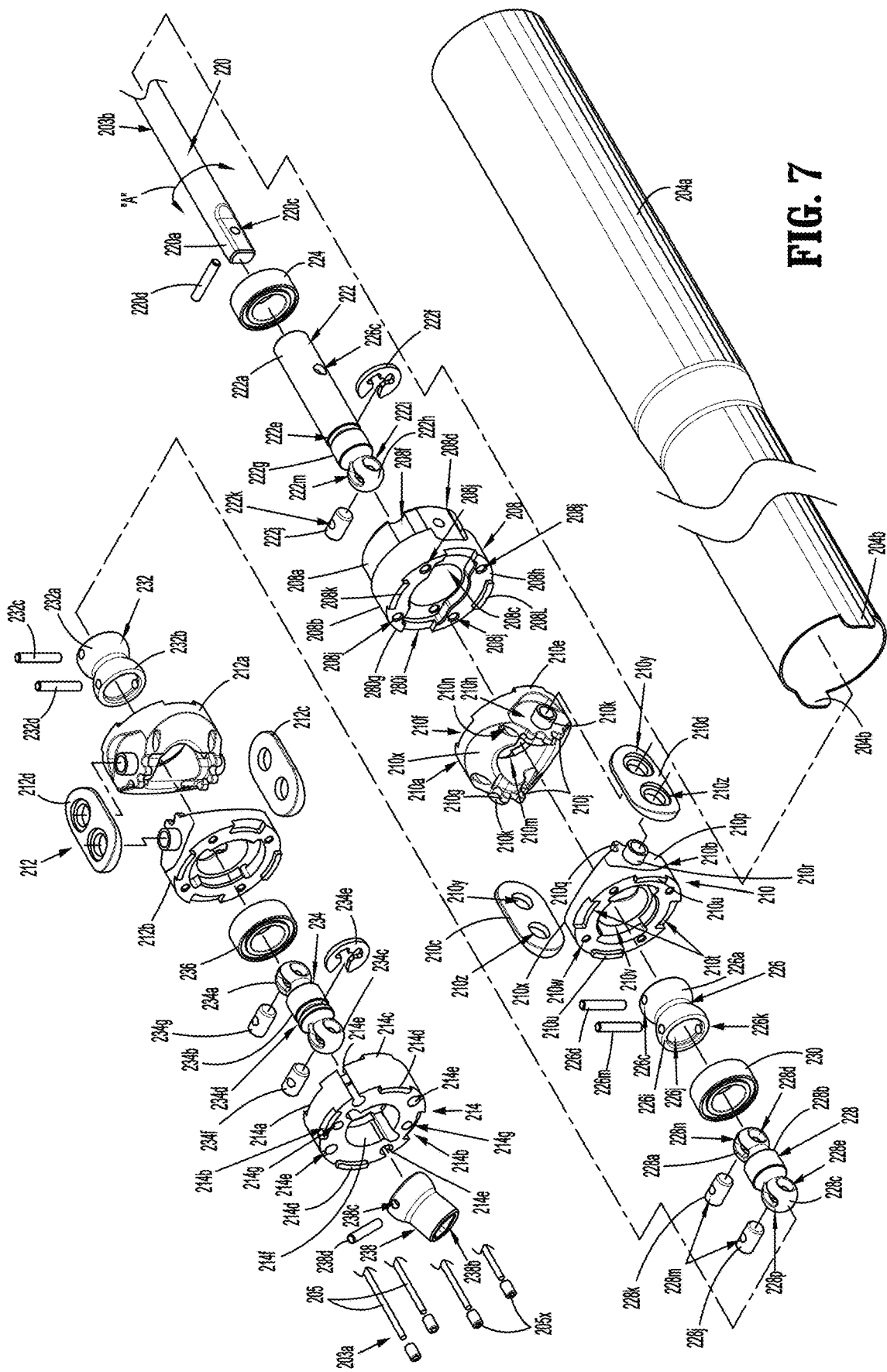
FIG. 7 is a perspective view, with parts separated, of the elongated shaft assembly of FIG. 4.
Figure 8:
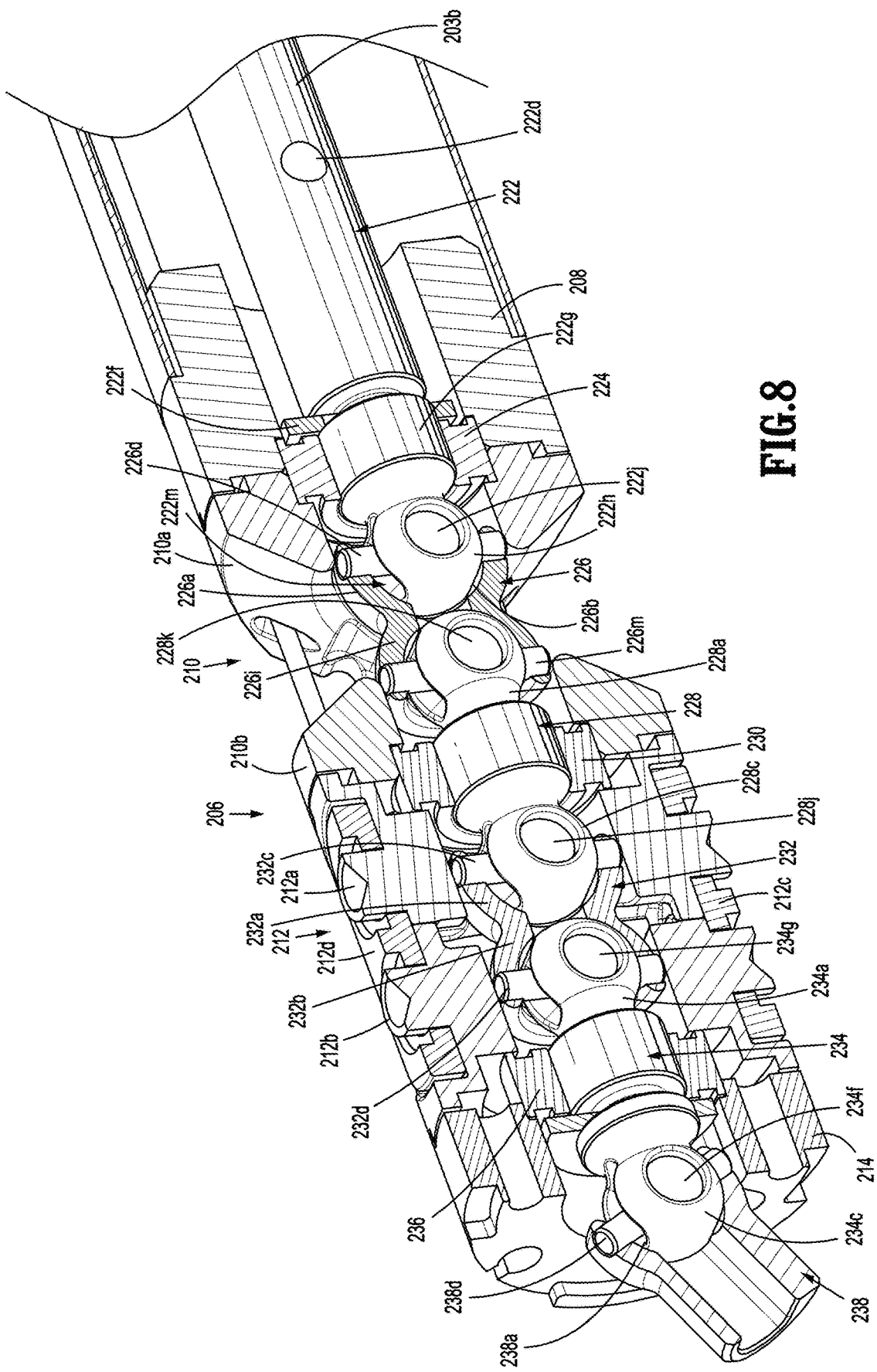
FIG. 8 is an enlarged, cross-sectional view of the wrist assembly of FIG. 5 as taken along section line 8-8 of FIG. 5

With reference to FIG. 7, first interface 208 of wrist assembly 206 is in the form of a tubular interface and includes a proximal housing 208a and a distal housing 208b that extends distally from proximal housing 208a, and a central aperture 208c that is defined therethrough to receive firing assembly 203b of drive assembly 203. Proximal housing 208a of first interface 208 defines a pair of side slots 208d (only one side slot 208d shown with the other identically disposed on the opposite side of proximal housing 208a) that receive distally extending tabs 204b of outer tube 204a. Proximal housing 208a further defines a plurality of cable channels 208f (e.g., four) disposed at circumferentially spaced apart locations about proximal housing 208a (only one cable channel 208f is explicitly shown). Distal housing 208b defines a first ledge 208g and a second ledge 208h that define a transverse channel 208i between the first and second ledges 208g, 208h. First and second ledges 208g, 208h define cable apertures 208j (e.g., two each) that align with cable channels 208f to receive cables 205 of cable drive assembly 203a of drive assembly 203 therethrough. First and second ledges 208g, 208h further include distal tabs 208k, 208L that extend distally therefrom.

Figure 9:
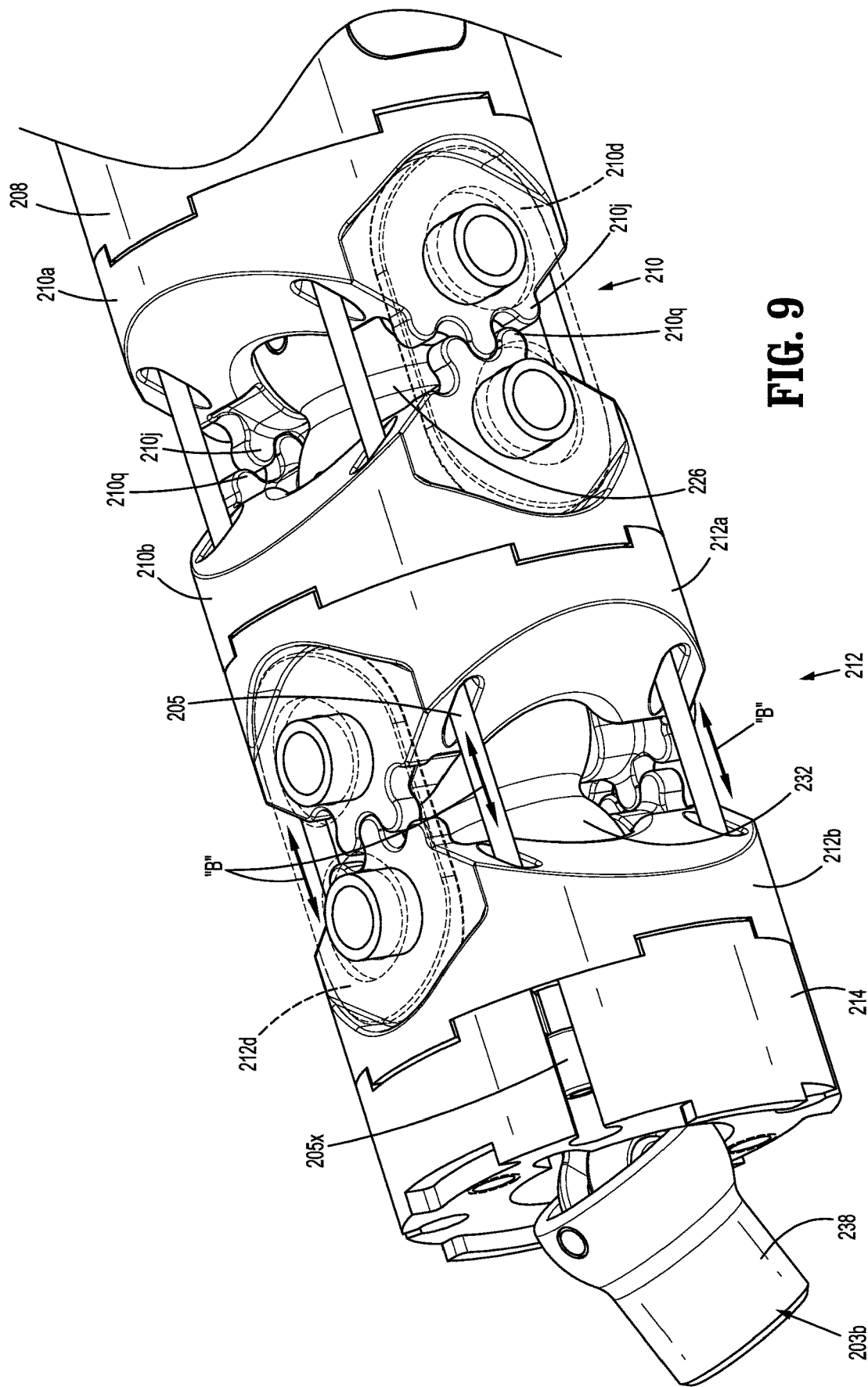
FIG. 9 is an enlarged view of the wrist assembly of FIG. 5 with portions thereof shown in phantom for clarity.

First joint 210 of wrist assembly 206 includes a proximal segment 210a and a distal segment 210b that are pivotally coupled together by links or caps 210c, 210d that help resist axial loading (created by tensile forces from cables 205) and misalignment in a transverse direction. In addition, links 210c, 210d help maintain clearance of, for instance, enmeshed gear teeth (see, e.g., FIG. 9 illustrating link 210d maintaining sufficient distance or axial separation between gear teeth 210j and 210q so that gear teeth 210j and 210q do not bind).

Proximal segment 210a of first joint 210 includes proximal tabs 210e (only one shown with an identical tab 210e shown on an opposite side of proximal segment 210a) that are received within transverse channel 208i of first interface 208. Proximal segment 210a defines a transverse recess 210f that is angularly displaced from proximal tabs 210e (e.g., 90 degrees) and positioned to receive distal tabs 208k, 208L of first interface 208 to prevent proximal segment 210a of first joint 210 from rotating relative to first interface 208 about longitudinal axis "L-L" (FIG. 2) (e.g., tongue and groove type interconnection). Proximal segment 210a includes a first coupler or gear 210g and a second coupler or gear 210h that extend distally from proximal segment 210 on opposed sides of proximal segment 210a. First and second gears 210g, 210h have a plurality of spaced apart teeth 210j. First and second gears 210g, 210h include pins 210k that extend laterally (e.g., perpendicularly) therefrom for engagement with links 210d, 210c of first joint 210. Any of the presently disclosed pins may include rivets or the like. Gears 210h, 210g are recessed from side surfaces of proximal segment 210a of first joint 210 to facilitate movement of links 210c, 210d of first joint 210 and distal segment 210b of first joint 210 relative to proximal segment 210a, as distal segment 210b articulates relative to proximal segment 210a. Proximal segment 210a of first joint 210 further defines a central opening 210m for receiving firing assembly 203b of drive assembly 203 therethrough, and a plurality of cable apertures 210n (e.g., four) for receiving the cables 205 of cable drive assembly 203a of drive assembly 203 therethrough.

Distal segment 210b of first joint 210 includes a coupler with knuckles or gears 210p (only one shown with a second identical coupler or gear 210p shown on an opposite side of distal segment 210b) that extend proximally from distal segment 210b and are positioned to enmesh or geometrically interlock (e.g., teeth 210q thereof) with first and second gears 210g, 210h of proximal segment 210a of first joint 210 to maintain rolling contact between respective interlocked gears (e.g., 210p, 210h; see FIGS. 7, 9 and 13) and to prevent an 'S' condition in the joint where the end effector location would be non-deterministic. Distal segment 210b further includes pins or bosses 210r (only one shown with a second identical pin 210r shown on an opposite side of distal segment 210b) that extend laterally from (e.g., perpendicularly from) gears 210p. Distal segment 210b further defines recesses 210t and includes distally extending tabs 210u that are alternately interspersed and disposed at angularly displaced locations (e.g., 90 degrees apart) about a distal end portion of distal end segment 210b. Distal segment 210b defines a central aperture 210v for receiving firing assembly 203b therethrough and a plurality of cable apertures 210w (e.g., four) for receiving cables 205 of cable drive assembly 203a therethrough.

Each of proximal and distal segments 210a, 210b of first joint 210 include a pair of tapered surfaces 210x that provide space between the distal and proximal segments 210a, 210b of first joint 210 to enable distal segment 210b to articulate relative to proximal segment 210a as teeth 210j, 210q of proximal and distal segments 210a, 210b enmesh with one another. Tapered surfaces 210x of proximal segment 210a are configured to contact tapered surfaces of distal segment 210b to limit articulation (e.g., define maximum articulation in a given direction) of distal segment 210b relative to proximal segment 210a.

Links 210c, 210d of first joint 210 define proximal and distal pin apertures 210y, 210z that receive pins 210k, 210r of proximal and distal segments 210a, 210b, respectively, to secure proximal and distal segments 210a, 210b of first joint 210 together and enable distal segment 210b to articulate relative to proximal segment 210a.

Second joint 212 of wrist assembly 206 is identical to first joint 210 of wrist assembly 206 but is angularly displaced (e.g., 90 degrees) relative to first joint 210 so that first and second joints 210, 212 can interconnect and articulate/pivot relative to one another. In particular, second joint 212 includes a proximal segment 212a and a distal segment 212b that are pivotally coupled together by links 212c, 212d such that proximal segment 212a, distal segment 212b, and links 212c, 212d of second joint 212 are identical to proximal segment 210a, distal segment 210b, and links 210c, 210d of first joint 210, respectively. Proximal segment 212a of second joint 212 is coupled to distal segment 210b of first joint 210 such that proximal segment 212a of second joint 212 is rotationally locked to distal segment 210b of first joint 210 (e.g., tongue and groove type interconnection). In this manner, proximal and distal segments 212a, 212b of second joint 212 can articulate/pivot relative to one another while distal segment 210b of first joint 210 articulates/pivots relative to proximal segment 210a of first joint 210.

Second interface 214 of wrist assembly 206 is in the form of a tubular interface and defines proximal and distal recesses 214a, 214b that correspond to, and/or are aligned with, one another, respectively. Second interface 214 includes proximal and distal tabs 214c, 214d that correspond to, and/or are aligned with, one another, respectively. Proximal recesses 214a and proximal tabs 214c of second interface 214 are configured to engage distally extending tabs 210u and recesses 210t of second joint 212 (e.g., tongue and groove type connection) to rotationally lock second interface 214 to distal segment 210b of second joint 212. Second interface 214 further defines cable slots 214e at circumferentially spaced apart locations about second interface 214 that are positioned to receive ferrules 205x and cables 205 therein to secure cables 205 to second interface 214. Second interface 214 further defines a central aperture 214f that is configured to receive firing assembly 203b of drive assembly 203 therethrough. Second interface 214 also defines alignment holes 214g to facilitate alignment and securement of wrist assembly 206 to end effector 300 of electromechanical surgical instrument 200.

With reference to FIGS. 7-14, firing assembly 203b of drive assembly 203 of electromechanical surgical instrument 200, which is in the form of a multi-stage universal joint assembly, includes a drive shaft 220, a ball shaft 222 that extends distally from drive shaft 220, a first bearing 224 supported on ball shaft 222 to rotatably support ball shaft 222, a first ball housing 226 coupled to a distal portion of ball shaft 222, a first dual ball shaft 228 coupled to first ball housing 226 and supporting a second bearing 230 that rotatably supports first dual ball shaft 228, a second ball housing 232 coupled to a distal portion of first dual ball shaft 228, a second dual ball shaft 234 coupled to a distal portion of second ball housing 232 and supporting a third bearing 236 that rotatably supports second dual ball shaft 234, and a drive coupler 238 supported on a distal portion of second dual ball shaft 234.

Drive shaft 220 of firing assembly 203b of drive assembly 203 has a proximal end portion coupled to a driven member 211 (FIG. 15) of drive assembly 203 that operably couples to one or more of motors 50 of robotic surgical assembly 100 (see FIGS. 1 and 15) to enable drive shaft 220 to rotate about longitudinal axis "L-L," as indicated by arrows "A" (FIG. 7). Drive shaft 220 extends to a keyed distal portion 220a configured to be received by a proximal portion of ball shaft 222. Keyed distal portion 220a is shown with a rectangular configuration, but may have any suitable non-circular configuration such as a triangle, square, star, etc. Keyed distal portion 220a defines a pin hole 220c configured to receive a pin 220d therein.

Ball shaft 222 of firing assembly 203b has proximal portion 222a defining a keyed bore 222b (FIG. 10) that is configured to receive keyed distal portion 220a of drive shaft 220 therein to enable ball shaft 222 to rotate with drive shaft 220. Keyed bore 222b can have any suitable non-circular configuration and may be configured to complement keyed distal portion 220a of drive shaft 220 to facilitate a rotatably locked connection between ball shaft 222 and drive shaft 220 such that ball shaft 222 and drive shaft 220 rotate together. Ball shaft 222 further defines a pin hole 222c that receives pin 220d therein to rotatably couple drive shaft 220 to ball shaft 222 (see FIGS. 7 and 11). Ball shaft 222 defines an annular clip channel 222e in an outer surface thereof. Annular clip channel 222e is configured to receive a clip 222f (e.g., an E-clip) to obstruct axial movement of first bearing 224 to enable first bearing 224 of firing assembly 203b to be maintained axially fixed on a bearing surface 222g of ball shaft 222. Ball shaft 222 further includes a ball member 222h supported on a distal end portion of ball shaft 222. Ball member 222h of ball shaft 222 defines a transverse opening 222i therethrough configured to receive a ball pin 222j defining a pin hole 222k therein. Ball member 222h further defines an elongated slot 222m that is configured to align with pin hole 222k of ball pin 222j.

First ball housing 226 of firing assembly 203b of drive assembly 203 has a proximal shell 226a defining a proximal bore 226b therein that rotatably receives ball member 222h of ball shaft 222 therein. Proximal shell 226a further defines a pin passage 226c that receives a pin 226d therethrough. Pin 226d is receivable within elongated slot 222m of ball member 222h of ball shaft 222 while received through proximal shell 226a of first ball housing 226 to rotatably couple ball member 222h of ball shaft 222 to proximal shell 226a of first ball housing 226 (see FIGS. 7 and 8) to define a universal joint and to enable pin 226d to move through elongated slot 222m of ball member 222h as first ball housing 226 articulates/pivots about ball member 222h (see, for example, articulation/pivoting indicated by arrows "D" in FIG. 16).

First ball housing 226 of firing assembly 203b also includes a distal shell 226i configured to couple to first dual ball shaft 228. Distal shell 226i defines a distal bore 226j and a pin passage 226k therethrough that receives a pin 226m therein to rotatably/articulatably couple first dual ball shaft 228 to distal shell 226i (e.g., to define another universal joint).

First dual ball shaft 228 of firing assembly 203b includes a proximal ball member 228a that extends proximally from a bearing support surface 228b, and a distal ball member 228c that extends distally from bearing support surface 228b that rotatably supports second bearing 230. Proximal and distal ball members 228a, 228c define transverse openings 228d, 228e therethrough, respectively, and elongated slots 228n, 228p therethrough, respectively. Transverse openings 228d, 228e of proximal and distal ball members 228a, 228c are configured to receive ball pins 228j, 228k therein, respectively. Each ball pin 228j, 228k defines a pin hole 228m therein. Pin hole 228m of ball pin 228k and elongated slot 228n of ball member 228a are configured to receive pin 226m of first ball housing 226 to rotatably/articulatably couple first dual ball shaft 228 to distal shell 226i of first ball housing 226 (e.g., to define universal joints).

Second ball housing 232 of firing assembly 203b of drive assembly 203 is identical to first ball housing 226 of firing assembly 203b and includes a proximal shell 232a, a distal shell 232b that extends distally from proximal shell 232a, and pins 232c, 232d that are received within proximal and distal shells 232a, 232b, respectively. Pins 232c, 232d of second ball housing 232 rotatably couple second ball housing 232 to ball members 228c, 234a of first dual ball shaft 228 and second dual ball shaft 234, respectively, (e.g., to define universal joints) similar to the rotatable/articulatable coupling described above with respect to first ball housing 226 and ball members 222h, 228a of ball shaft 222 and first dual ball shaft 228, respectively.

Second dual ball shaft 234 of firing assembly 203b of drive assembly 203 is similar to first dual ball shaft 228 of firing assembly 203b and includes a proximal ball member 234a that extends proximally from a bearing support surface 234b that supports third bearing 236, and a distal ball member 234c that extends distally from bearing support surface 234b. Bearing support surface 234b further defines an annular clip channel 234d that is configured to receive a clip 234e (e.g., an E-clip) to obstruct axial movement of third bearing 236 and axially support third bearing 236 on bearing support surface 234b of second dual ball shaft 234. Second dual ball shaft 234 further includes ball pins 234f, 234g. Proximal ball member 234a of second dual ball shaft 234 is rotatably coupled to distal shell 232b of second ball housing 232 (e.g., a universal joint) and distal ball member 234c of second dual ball shaft 234 rotatably supports drive coupler 238 thereon.

Drive coupler 238 of firing assembly 203b defines a proximal bore 238a (FIG. 8) that rotatably receives distal ball member 234c of second dual ball shaft 234, and a distal bore 238b that is configured to couple to end effector 300 of electromechanical surgical instrument 200. Although distal bore 238b of drive coupler 238 is shown including a non-circular configuration, such as a D-shaped configuration, distal bore 238b can have any non-circular configuration (e.g., triangular, rectangular, pentagonal, etc.) to facilitate a rotatably locked connection between firing assembly 203b and end effector 300 so that end effector 300, or components thereof, can rotate with firing assembly 203b of drive assembly 203. Drive coupler 238 further defines a pin hole 238c that receives a pin 238d to rotatably couple drive coupler 238 to distal ball member 234c of second dual ball shaft 234.

With reference to FIG. 3, end effector 300 of electromechanical surgical instrument 200 includes a mounting portion 302 on a proximal end portion thereof, and a first jaw member 304 (e.g., an anvil) and a second jaw member 306 (e.g., a cartridge assembly) that are coupled to mounting portion 302. First and second jaw members 304, 306 are positioned for pivotal movement between open (FIG. 3) and closed (not shown) positions. First and second jaw members 304, 306 support a drive assembly 308 that is configured to fire a fastener cartridge 310 supported in second jaw member 306.

As seen in FIG. 4, mounting portion 302 of end effector 300 includes mounting tabs 302a and defines mounting recesses 302b that engage respective distal recesses 214b and distal tabs 214d of second interface 214 of wrist assembly 206. Mounting portion 302 further includes alignment pins 302 that are received within alignment holes 214g of second interface 214 of wrist assembly 206. Mounting portion 302 further defines a central opening 302d that is configured to receive drive coupler 238 of firing assembly 203b to couple drive coupler 238 to drive assembly 308 of end effector 300.

Figure 10:
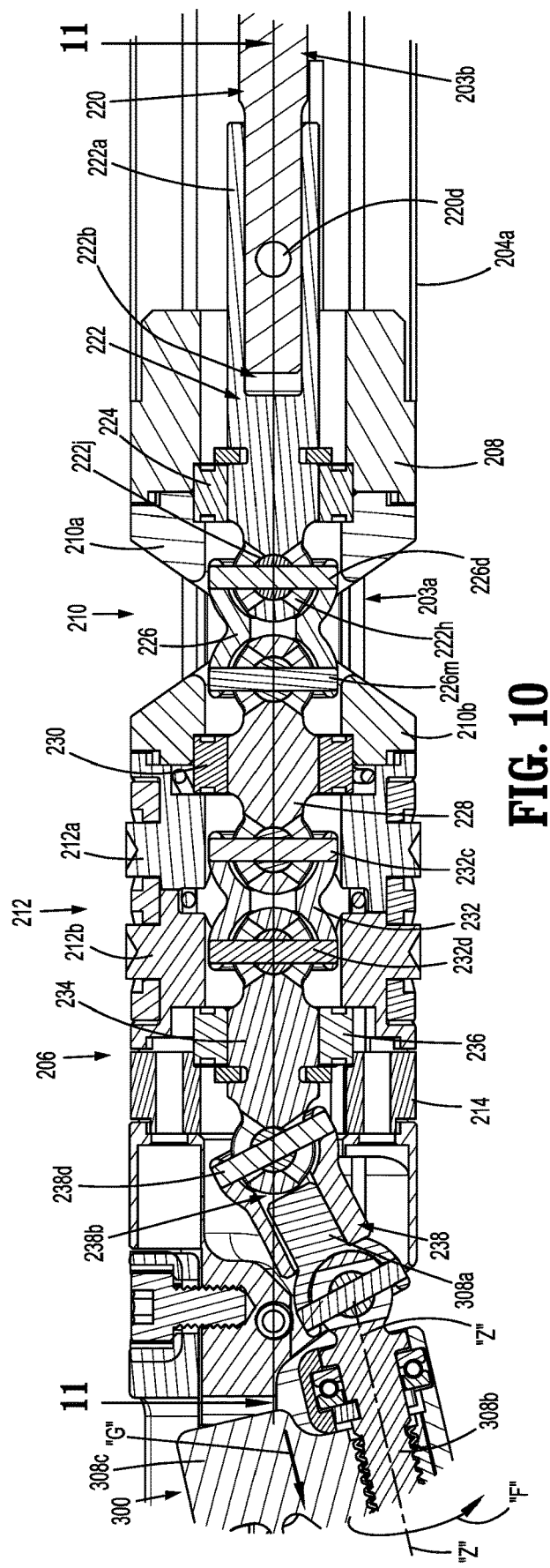
FIG. 10 is an enlarged, longitudinal, cross-sectional view of the indicated area of detail shown in FIG. 2.
Figure 11:
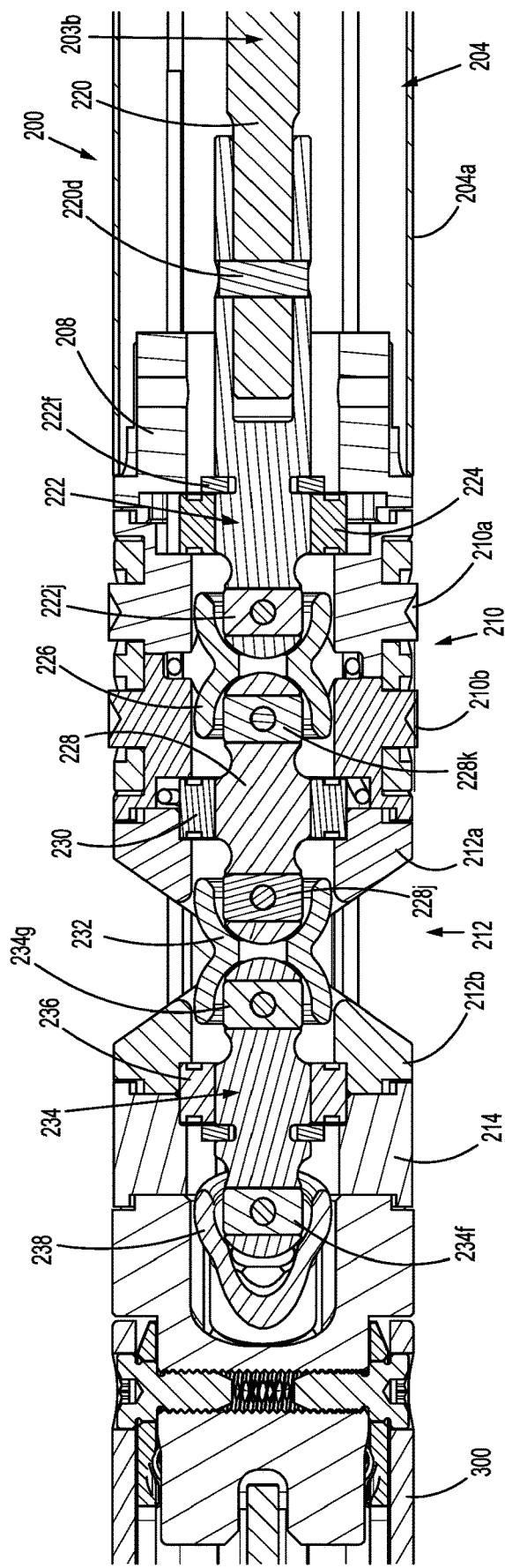
FIG. 11 is a cross-sectional view of the wrist assembly of FIG. 5 as taken along the section line 11-11 of FIG. 10.
Figure 14:
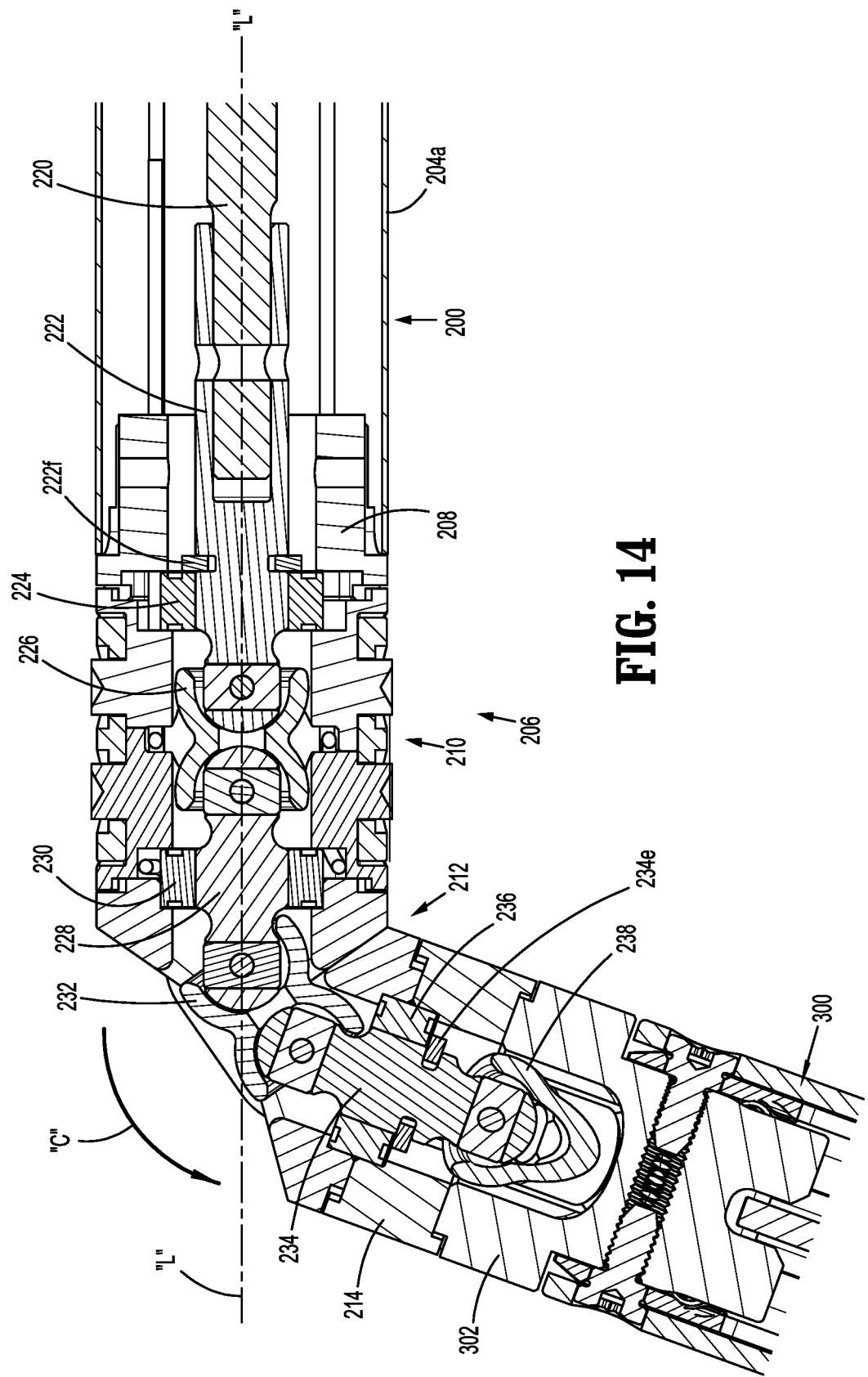
FIG. 14 is a longitudinal, cross-sectional view of FIG. 13.

With reference to FIG. 10, drive assembly 308 of end effector 300 includes a driven coupler 308a that is received in distal bore 238b of drive coupler 238 of firing assembly 203b of drive assembly 203. Driven coupler 308a of drive assembly 308 includes a non-circular configuration (e.g., D-shape) that is keyed to distal bore 238b of drive coupler 238 of firing assembly 203b so that driven coupler 308a and drive coupler 238 are rotatably locked with respect to one another such that driven coupler 308a and drive coupler 238 rotate together as drive coupler 238 rotates. Driven coupler 308a is pinned to a lead screw 308b that supports a drive beam 308c such that rotation of driven coupler 308a causes lead screw 308b to rotate and axially advance drive beam 308c along lead screw 308b. For a more detailed description of components of example end effectors similar to end effector 300, reference can be made to U.S. Patent Application Publication Nos. 2016/0242779 and 2015/0297199, the entire disclosures of each of which are incorporated by reference herein.

Figure 16:
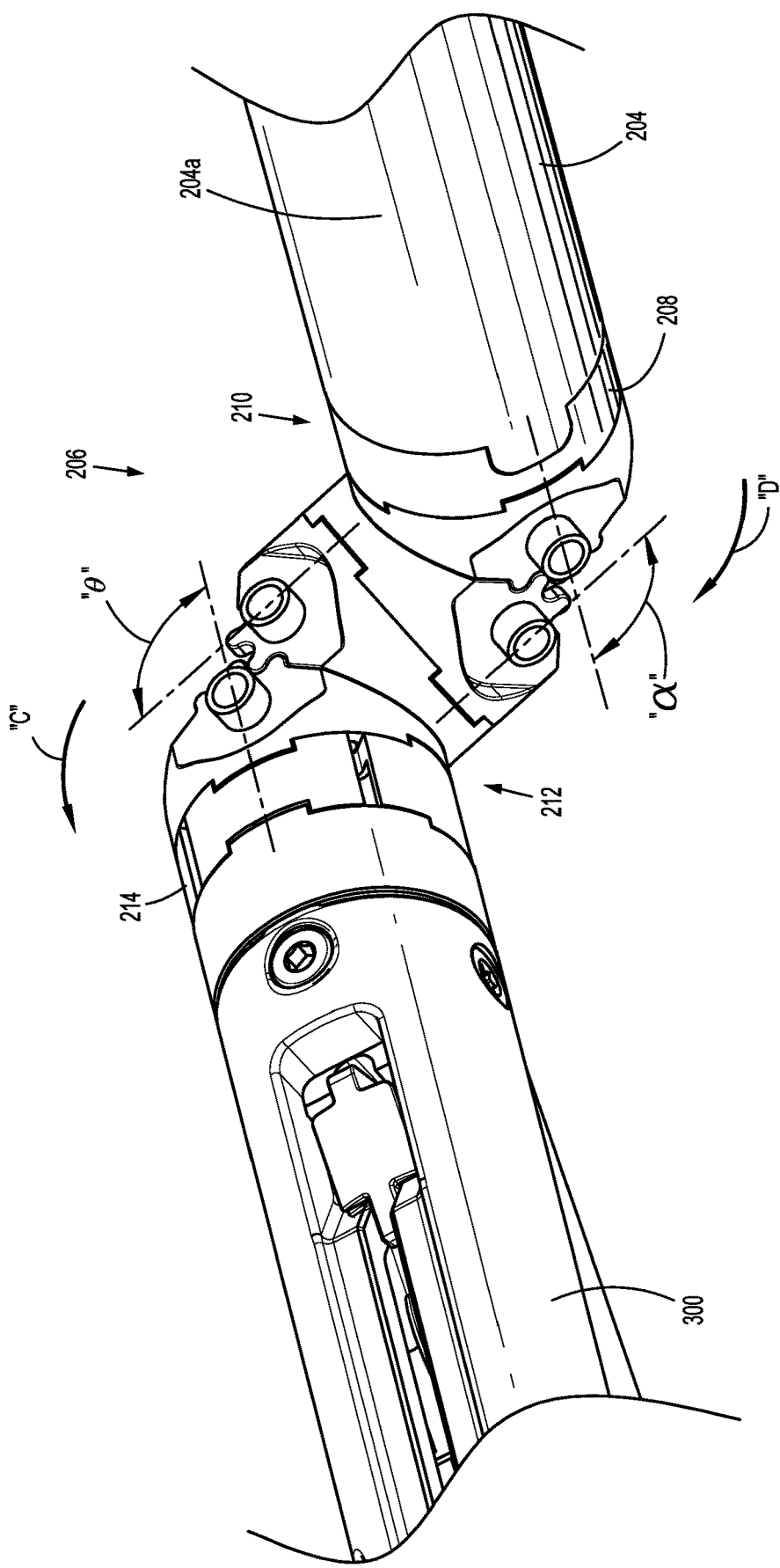
FIG. 16 is an enlarged view of the indicated area of detail shown in FIG. 15 with portions thereof removed for clarity.
Figure 17:
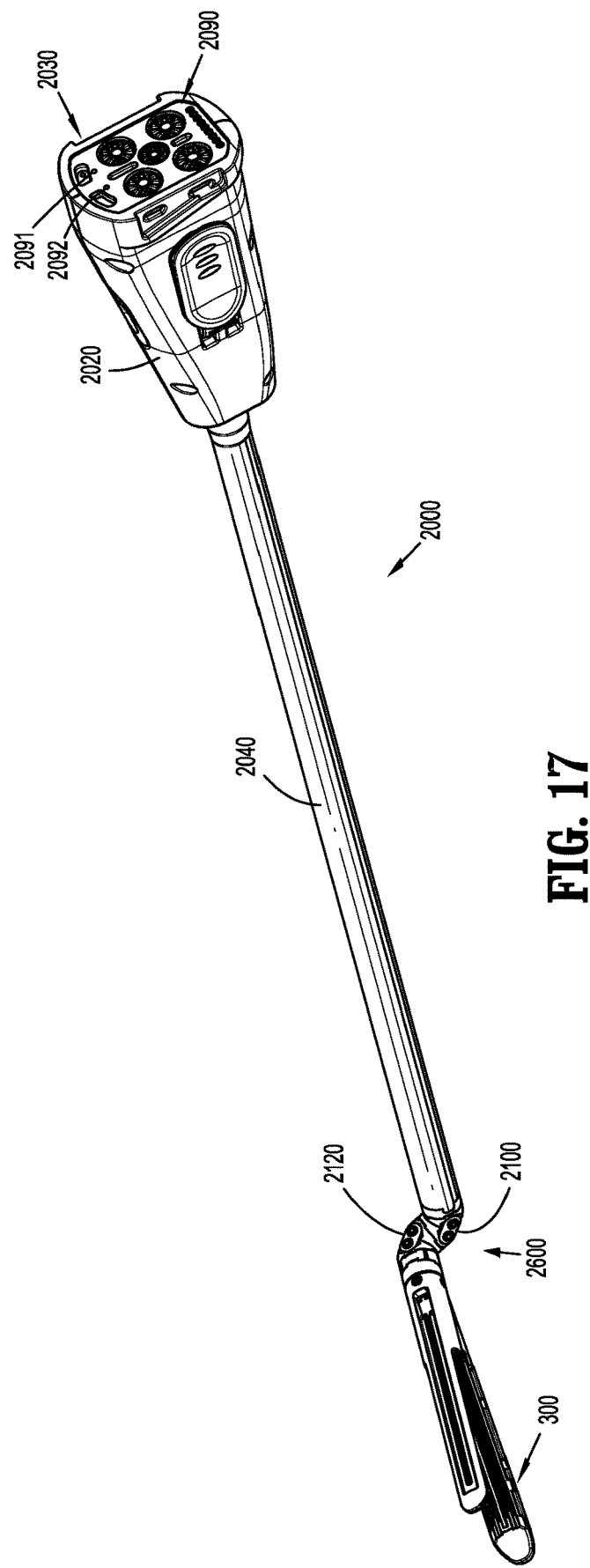
FIG. 17 is a perspective view of an alternative embodiment of a surgical instrument shown in an exemplary articulated position.
Figure 18:
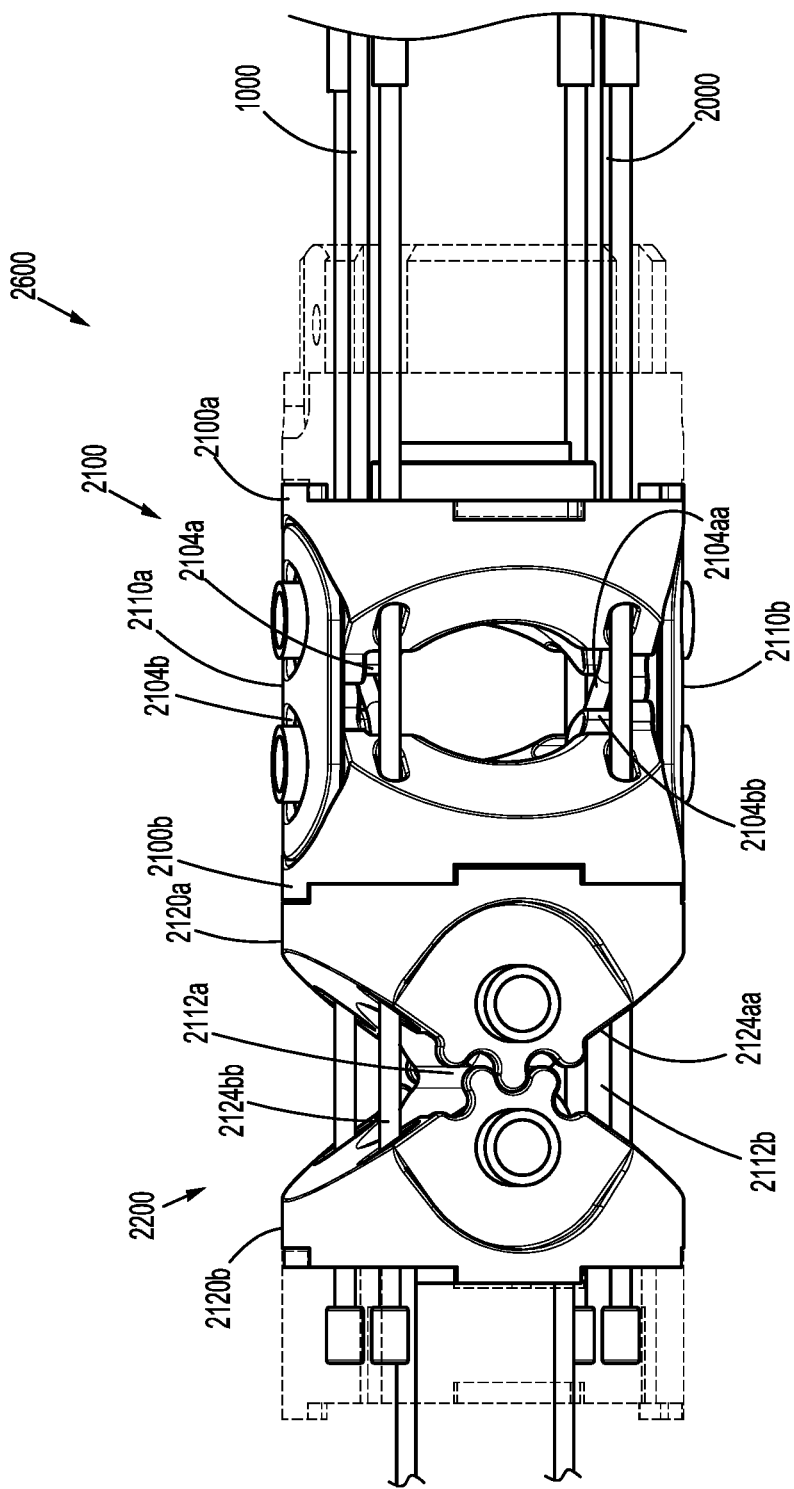
FIG. 18 is a perspective view of a wrist assembly of the surgical instrument of FIG. 17.

In use, with electromechanical surgical instrument 200 coupled to robotic surgical assembly 100 as seen in FIG. 1, one or more motors 50 of instrument drive unit 110 can be actuated to rotate one or more of driven members 209 of electrosurgical instrument 200 to push and/or pull one or more cables 205 of cable drive assembly 203a of drive assembly 203 of electromechanical surgical instrument 200. As cables 205 of cable drive assembly 203a axially translate, as indicated by arrows "B" (FIG. 9), one or both of first and second joints 210, 212 of wrist assembly 206 rotate and/or articulate with one or more of first ball housing 226, first dual ball shaft 228, second ball housing 232, and/or second dual ball shaft 234 of firing assembly 203b of drive assembly 203, relative to longitudinal axis "L-L," as indicated by arrows "C" and "D" (see FIGS. 12-16). Each of first and second joints 210, 212 can be configured to articulate through an articulation angle of up to 70 degrees such that first joint 210 can be articulated through an articulation angle "α" up to 70 degrees while second joint 212 is articulated through an articulation angle "Θ" up to 70 degrees, as seen in FIG. 16. As can be appreciated, one or more components of firing assembly 203b (e.g., first ball housing 226, first dual ball shaft 228, second ball housing 232, and/or second dual ball shaft 234, etc.) pivot, rotate, and/or articulate as first and second joint 210, 212 pivot, rotate, and/or articulate.

While first and/or second joints 210, 212 of wrist assembly 206 are disposed in an articulated (FIGS. 12-16) or an unarticulated position (FIG. 2), firing assembly 203b can be rotated about longitudinal axis "L-L," as indicated by arrows "A," (see FIGS. 2 and 7) in response to rotation of driven member 211 (FIG. 15) by one or more of motors 50 of instrument drive unit 110 (FIG. 1). Rotation of firing assembly 203b of drive assembly 203 causes drive coupler 238 of firing assembly 203b to rotate lead screw 308b of end effector 300 about its axis, e.g., axis "Z-Z," as indicated by arrows "F" (FIG. 10). Rotation of lead screw 308b of end effector 300 causes drive beam 308c of end effector 300 to advance distally along lead screw 308b, as indicated by arrow "G," so that first and second jaw members 304, 306 of end effector 300 move from the open or unapproximated position (FIG. 3) thereof to the closed or approximated position (not shown) thereof. As drive beam 308c of end effector 300 continues to advance distally along first and second jaw members 304, 306, drive beam 308c fires fastener cartridge 310 (FIG. 3) to fasten and/or sever tissue captured between first and second jaw members 304, 306 similar to that described in U.S. Patent Application Publication No. 2015/0297199 referenced above.

Turning now to FIGS. 17, 18, 19A-19C, and 20A-20C, an alternative embodiment of an electromechanical surgical instrument is shown and described as electromechanical surgical instrument 2000. Electromechanical surgical instrument 2000 is similar to electromechanical surgical instrument 200, described above, includes all of the same features and components as electromechanical surgical instrument 200, and is usable with (and interfaces with) surgical system 1 (FIG. 1) in the same manner as electromechanical surgical instrument 200. However, electromechanical surgical instrument 2000 additionally includes electrical cables 1000, 2000, and wrist assembly 2600 and housing 2020 for supporting electrical cables 1000, 2000. Accordingly, for brevity, only the basic components of electromechanical surgical instrument 2000, and the differences between electromechanical surgical instrument 2000 and electromechanical surgical instrument 200, will be described.

As described in detail below, wrist assembly 2600 includes structural features that facilitate passage of electrical cables 1000, 2000 therethrough with minimal resistance and minimal stress imparted on electrical cables 1000, 2000 during articulation of wrist assembly 2600. Despite high articulation of the components of wrist assembly 2600, electrical cables 1000, 2000 do not translate longitudinally through any of joints 2100, 2120. This eliminates the need for tensioning or payout mechanisms that would otherwise be required to drive any cables or wires during articulation. Elimination of longitudinal translation of electrical cables 1000, 2000 also reduces the possibility of failures due to wear and abrasion of electrical cables 1000, 2000 and any components in contact with electrical cables 1000, 2000. Additionally, electrical cables 1000, 2000 bend through only a single axis during articulation of the wrist assembly 2600, as opposed to being bent in multiple directions, which significantly extends the lifetime of the electrical cables 1000, 2000 and even the components the electrical cables 1000, 2000 are in contact with. Additionally, the electrical cables 1000, 2000 are positioned within the wrist assembly 2600, beneath drive cabling and shielding structures throughout the full articulation range, which reduces chances of damage to the electrical cables 1000, 2000 from incidental contact and reprocessing.

Electromechanical surgical instrument 2000 of robotic surgical system 1 (FIG. 1) includes a housing 2020 at a proximal end portion thereof and an elongated shaft 2040 that extends distally from housing 2020. A wrist assembly 2600 is supported on a distal end portion of elongated shaft 2040 that couples end effector 300 to elongated shaft 2040.

Housing 2020 of electromechanical surgical instrument 2000 is configured to selectively couple to instrument drive unit 110 of robotic surgical assembly 100 (FIG. 1), for example, via side loading on a sterile interface module 112 of robotic surgical assembly 100, to enable motors 50 of instrument drive unit 110 of robotic surgical assembly 100 to operate end effector 300 of electromechanical surgical instrument 2000. Housing 2020 of electromechanical surgical instrument 2000 supports a drive assembly 2030 (including cable drive assembly 2030a and firing assembly 2030b) that mechanically and/or electrically cooperates with motors 50 of instrument drive unit 110 of robotic surgical assembly 100. Additionally, housing 2020 includes a first electrical contact 2091 on a proximal portion thereof which interfaces with a corresponding electrical contact (not shown) of instrument drive unit 110 to create an electrical connection between electrical cable 1000 and the other components of robotic surgical system 1 (e.g., an electrosurgical generator, controller, sensor, etc.). Housing 2020 similarly includes a second electrical contact 2092 on a proximal portion thereof which interfaces with a corresponding electrical contact (not shown) of instrument drive unit 110 to create an electrical connection between electrical cable 2000 and the other components of robotic surgical system 1 (e.g., an electrosurgical generator, controller, sensor, etc.). It is contemplated that electromechanical surgical instrument 2000 may additionally include a printed circuit board (not shown) to which electrical cable 1000 and/or electrical cable 2000 are coupled.

Electrical cables 1000, 2000 may be utilized to create an electrical connection between any portion of electromechanical surgical instrument 2000 (e.g., end effector 300) and any component(s) of robotic surgical system 1 (e.g., robotic arms 2, 3, control device 4, and/or operating console 5). In one aspect, at least one of electrical cables 1000, 2000 is used to transmit electrosurgical treatment energy from an electrosurgical generator "G" (see FIG. 1) to a portion of end effector 300, such as an energy delivery portion or device (not shown) coupled to end effector 300. Additionally, one or both of electrical cables 1000, 2000 may be utilized to transmit sensor signals between end effector 300 (or sensors coupled thereto) and any other component(s) of robotic surgical system 1.

Wrist assembly 2600 is supported on elongated shaft 2040 and includes a first joint 2100 coupled to a second joint 2120. First joint 2100 includes a proximal segment 2100a defining a proximal arcuate surface 2104a and a distal segment 2100b defining a distal arcuate surface 2104b on each side thereof. Proximal segment 2100a is coupled to distal segment 2100b via a pair of links 2110a, 2110b. Similarly, second joint 2120 includes a proximal segment 2120a defining a proximal arcuate surface 2124a and a distal segment 2120b defining a distal arcuate surface 2124b on each side thereof. Proximal segment 2120a is coupled to distal segment 2120b via a pair of links 2112a, 2112b.

As described above with respect to wrist assembly 260, an end effector 300 is coupled to wrist assembly 2600 and a plurality of cables are coupled to the wrist assembly 2600 to manipulate first joint 2100 and second joint 2120 to enable wrist assembly 2600 to articulate relative to the longitudinal axis "L" (FIG. 2) defined by elongated shaft 2040.

Electrical cables 1000, 2000 pass through first joint 2100 and second joint 2200 of wrist assembly 2600, and the distal portion of each of electrical cables 1000, 2000 couple to end effector 300. In particular, proximal segment 2100a of first joint 2100 defines a proximal aperture 2102a and distal segment 2100b of first joint 2100 defines a distal aperture 2102b, which is misaligned with the proximal aperture 2102a. Similarly, proximal segment 2120a of second joint 2120 defines a proximal aperture 2122a and distal segment 2120b of second joint 2120 defines a distal aperture 2122b, which is misaligned with the proximal aperture 2122a. Electrical cable 1000 passes through proximal aperture 2102a defined by the proximal segment 2100a of first joint 2100, distal aperture 2102b defined by distal segment 2100b of first joint 2100, proximal aperture 2122a defined by proximal segment 2120a of second joint 2120, and distal aperture 2122b defined by distal segment 2120b of second joint 2120. Similarly, electrical cable 2000 passes through respective apertures defined on the other side of first joint 2100 and second joint 2120, respectively.

With respect to first joint 2100, and with particular reference to FIGS. 19A-19C, proximal arcuate surface 2104a, proximal aperture 2102a, distal arcuate surface 2104b, and distal aperture 2102b are positioned and dimensioned such that, during articulation of wrist assembly 2600, electrical cable 1000 rolls off of distal arcuate surface 2104b when electrical cable 1000 rolls on to proximal arcuate surface 2104a, and electrical cable 1000 rolls off of proximal arcuate surface 2104a when electrical cable 1000 rolls on to distal arcuate surface 2104b. With this configuration, it is possible to position electrical cable 1000 between proximal segment 2100a and distal segment 2100b such that, as distal segment 2100b articulates relative to proximal segment 2100a, electrical wire 1000 rolls onto distal arcuate surface 2104b at the same rate that it is rolled off of proximal arcuate surface 2104a. Thus, during articulation, stress imparted on one portion of electrical cable 1000 within the first joint 2100 is always accompanied by counteracting relief of stress on another portion of electrical cable 1000 within the first joint 2100.

Electrical cable 2000 is similarly arranged with similar arcuate surfaces present on the other side of proximal segment 2100a and distal segment 2100b of first joint 2100. In particular, the proximal segment 2100a of first joint 2100 defines a second proximal arcuate surface 2104aa (FIG. 18) on the other side thereof, and distal segment 2100b of first joint 2100 defines a second distal arcuate surface 2104bb on the other side thereof. Second electrical cable 2000 is positioned such that, during articulation of wrist assembly 2600, second electrical cable 2000 rolls off of second distal arcuate surface 2104bb as electrical cable 2000 rolls on to second proximal arcuate surface 2104aa, and second electrical cable 2000 rolls off of second proximal arcuate surface 2104aa as second electrical cable 2000 rolls on to second distal arcuate surface 2104bb.

Figure 20C:
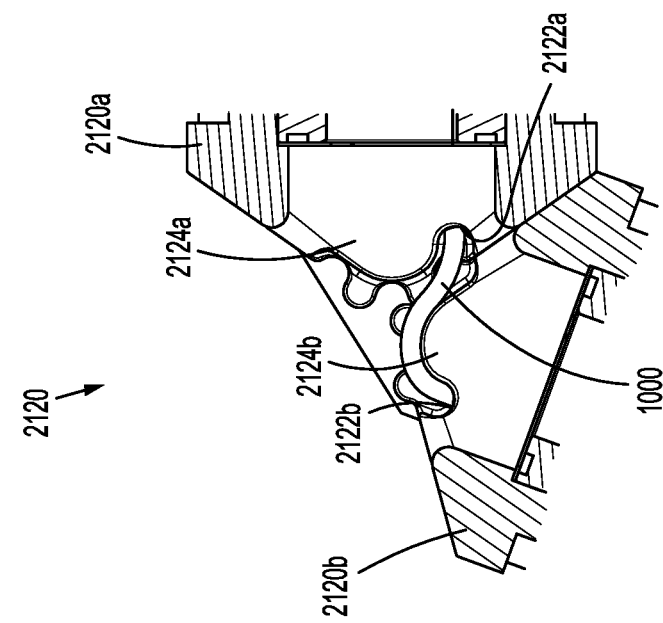
FIG. 20C is a cross-sectional view of the second joint of the wrist assembly of FIG. 18 in another articulated position.
Figure 20B:
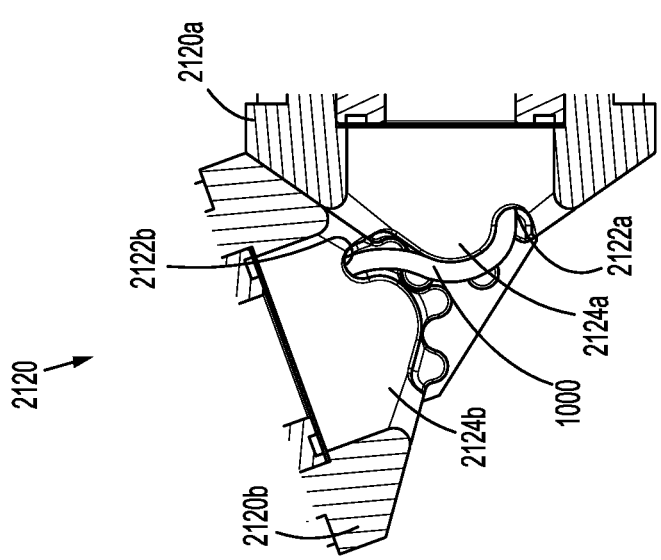
FIG. 20B is a cross-sectional view of the second joint of the wrist assembly of FIG. 18 in an articulated position.
Figure 20A:
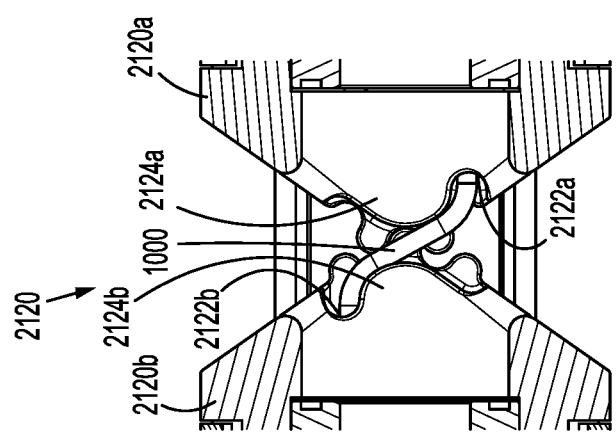
FIG. 20A is a cross-sectional view of a second joint of the wrist assembly of FIG. 18 in an unarticulated position.

With respect to second joint 2120, and with particular reference to FIGS. 20A-20C, proximal arcuate surface 2124a, proximal aperture 2122a, distal arcuate surface 2124b, and distal aperture 2122b are positioned and dimensioned such that, during articulation of wrist assembly 2600, electrical cable 1000 rolls off of distal arcuate surface 2124b when electrical cable 1000 rolls on to proximal arcuate surface 2124a, and electrical cable 1000 rolls off of proximal arcuate surface 2124a when electrical cable 1000 rolls on to distal arcuate surface 2124b. With this configuration, it is possible to position electrical cable 1000 between proximal segment 2120a and distal segment 2120b such that as distal segment 2120b articulates relative to proximal segment 2120a, electrical wire 1000 rolls onto distal arcuate surface 2124b at the same rate that it is rolled off of proximal arcuate surface 2124a. Thus, during articulation, stress imparted on one portion of electrical cable 1000 is always accompanied by counteracting relief of stress on another portion of electrical cable 1000.

Electrical cable 2000 is similarly arranged with similar arcuate surfaces present on the other side of proximal segment 2120a and distal segment 2120b of second joint 2120. In particular, proximal segment 2120a of second joint 2120 defines a second proximal arcuate surface 2124aa (FIG. 18) on the other side thereof, and distal segment 2120b of second joint 2120 defines a second distal arcuate surface 2124bb on the other side thereof. Second electrical cable 2000 is positioned such that during articulation of wrist assembly 2600 second electrical cable 2000 rolls off of second distal arcuate surface 2124bb, as electrical cable 2000 rolls on to second proximal arcuate surface 2124aa and second electrical cable 2000 rolls off of second proximal arcuate surface 2124aa as second electrical cable 2000 rolls on to second distal arcuate surface 2124bb.

FIG. 19A illustrates first joint 2100 of wrist assembly 2600 in an unarticulated position. In this position, electrical wire 1000 is in contact with both arcuate surface 2104a of proximal segment 2100a and arcuate surface 2104b of distal segment 2100b. When first joint 2100 is transitioned from an unarticulated position (FIG. 19A) to one fully articulated position (FIG. 19B), electrical cable 1000 contacts a larger area of arcuate surface 2014a and is no longer in contact with arcuate surface 2104b. Likewise, when first joint 2100 is transitioned from an unarticulated position (FIG. 19A) to another fully articulated position (FIG. 19C), electrical cable 1000 is no longer in contact with arcuate surface 2104a and contacts a larger area of arcuate surface 2104b. As first joint 2100 transitions between the unarticulated position and the multiple articulated positions, electrical cable 1000 bends through only one axis, as opposed to bending in multiple directions, which extends its lifetime. Although not shown, electrical cable 2000 similarly interacts with arcuate surfaces on the other side of first joint 2100 as first joint 2100 transitions between the unarticulated position and the multiple articulated positions.

FIG. 20A illustrates second joint 2120 of wrist assembly 2600 in an unarticulated position. In this position, electrical wire 1000 is in contact with both arcuate surface 2124a of proximal segment 2120a and arcuate surface 2124b of distal segment 2120b. When second joint 2120 is transitioned from an unarticulated position (FIG. 20A) to one fully articulated position (FIG. 20B), electrical cable 1000 contacts a larger area of arcuate surface 2024a and is no longer in contact with arcuate surface 2124b. Likewise, when second joint 2120 is transitioned from an unarticulated position (FIG. 20A) to another fully articulated position (FIG. 20C), electrical cable 1000 is no longer in contact with arcuate surface 2124a and contacts a larger area of arcuate surface 2124b. As second joint 2120 transitions between the unarticulated position and the multiple articulated positions, electrical cable 1000 bends through only one axis, as opposed to bending in multiple directions, which extends its lifetime. Although not shown, electrical cable 2000 similarly interacts with arcuate surfaces on the other side of second joint 2120 as the second joint 2120 transitions between the unarticulated position and the multiple articulated positions.

Although electromechanical surgical instrument 200, 2000 is described herein in connection with robotic surgical system 1, the presently disclosed electromechanical surgical instruments 200, 2000 can be provided in the form of a hand held electromechanical instrument, which may be manually driven and/or powered. For instance, U.S. Patent Application Publication No. 2015/0297199, referenced above, describes one example of a powered hand held electromechanical instrument, one or more of the components of which (e.g., the surgical device or handle thereof) can be utilized in connection with the presently disclosed surgical instrument 200, 2000.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

The invention claimed is:

1. A robotic electromechanical surgical instrument, comprising:
a housing;
an elongated shaft defining a longitudinal axis and extending distally from the housing;
a wrist assembly supported on the elongated shaft and including a first joint coupled to a second joint, the first joint including a proximal segment defining a proximal arcuate surface and a distal segment defining a distal arcuate surface;
an end effector coupled to the wrist assembly;
a plurality of cables, each cable of the plurality of cables having a distal end coupled to the distal segment of the wrist assembly, the plurality of cables distally and proximally movable through the elongated shaft and the wrist assembly to manipulate the first and second joints to enable the wrist assembly to articulate relative to the longitudinal axis; and
an electrical cable extending between the housing and the end effector, wherein the electrical cable extends through the wrist assembly so as to not translate through the wrist assembly, the electrical cable positioned relative to the proximal arcuate surface and the distal arcuate surface such that, during articulation of the wrist assembly, the electrical cable rolls off of the distal arcuate surface as the electrical cable rolls on to the proximal arcuate surface, and the electrical cable rolls off of the proximal arcuate surface as the electrical cable rolls on to the distal arcuate surface.

2. The robotic electromechanical surgical instrument of claim 1, wherein the proximal and distal segments of the first joint are supported for movement relative to one another to facilitate articulation of the wrist assembly relative to the longitudinal axis of the elongated shaft.

3. The robotic electromechanical surgical instrument of claim 1, wherein the proximal segment defines a proximal aperture and the distal segment defines a distal aperture, the electrical cable disposed through the proximal aperture and the distal aperture.

4. The robotic electromechanical surgical instrument of claim 1, wherein the electrical cable is positioned between the proximal segment and the distal segment such that, as the distal segment articulates relative to the proximal segment, the electrical cable rolls onto the distal arcuate surface at a rate and the electrical cable rolls off of the proximal arcuate surface at the rate.

5. The robotic electromechanical surgical instrument of claim 1, wherein the electrical cable is configured to transmit electrosurgical treatment energy to a portion of the end effector.

6. The robotic electromechanical surgical instrument of claim 1, wherein the electrical cable is configured to transmit a sensor signal from the end effector.

7. The robotic electromechanical surgical instrument of claim 1, further comprising a link coupling the proximal segment of the first joint to the distal segment of the first joint.

8. The robotic electromechanical surgical instrument of claim 1, wherein the second joint includes a proximal segment defining a proximal arcuate surface and a distal segment defining a distal arcuate surface.

9. The robotic electromechanical surgical instrument of claim 8, wherein the electrical cable is positioned relative to the proximal arcuate surface of the second joint and the distal arcuate surface of the second joint such that, during articulation of the wrist assembly, the electrical cable rolls off of the distal arcuate surface of the second joint as the electrical cable rolls on to the proximal arcuate surface of the second joint, and the electrical cable rolls off of the proximal arcuate surface of the second joint as the electrical cable rolls on to the distal arcuate surface of the second joint.

10. The robotic electromechanical surgical instrument of claim 1, further comprising a second electrical cable, wherein the proximal segment of the first joint defines a second proximal arcuate surface, the distal segment of the first joint defines a second distal arcuate surface, and the second electrical cable is positioned such that, during articulation of the wrist assembly, the second electrical cable rolls off of the second distal arcuate surface as the electrical cable rolls on to the second proximal arcuate surface, and the second electrical cable rolls off of the second proximal arcuate surface as the second electrical cable rolls on to the second distal arcuate surface.

11. The robotic electromechanical surgical instrument of claim 1, wherein the housing includes an electrical contact disposed thereon and the electrical cable is coupled to the electrical contact.

12. A wrist assembly for use with an electromechanical surgical instrument, the wrist assembly comprising:
a first joint including a proximal segment defining a proximal arcuate surface and a distal segment defining a distal arcuate surface;
a second joint operably coupled to the first joint;
a plurality of cables, each cable of the plurality of cables having a distal end coupled to at least one of the first joint or the second joint, the plurality of cables distally and proximally movable through the wrist assembly to manipulate the first and second joints to enable the wrist assembly to articulate relative to a longitudinal axis defined by the wrist assembly in an unarticulated position; and
an electrical cable extending through the wrist assembly, wherein the electrical cable extends through the wrist assembly so as to not translate through the wrist assembly, the electrical cable being positioned relative to the proximal arcuate surface and the distal arcuate surface such that, during articulation of the wrist assembly, the electrical cable rolls off of the distal arcuate surface as the electrical cable rolls on to the proximal arcuate surface, and the electrical cable rolls off of the proximal arcuate surface as the electrical cable rolls on to the distal arcuate surface.

13. The wrist assembly of claim 12, wherein the proximal segment defines a proximal aperture and the distal segment defines a distal aperture, the electrical cable disposed through the proximal aperture and the distal aperture.

14. The wrist assembly of claim 12, wherein the electrical cable is positioned between the proximal segment and the distal segment such that, as the distal segment articulates relative to the proximal segment, the electrical cable rolls onto the distal arcuate surface at a rate and the electrical cable rolls off of the proximal arcuate surface at the rate.

15. The wrist assembly of claim 12, wherein the electrical cable is configured to transmit electrosurgical treatment energy to a portion of an end effector supported by the wrist assembly.

16. The wrist assembly of claim 12, wherein the electrical cable is configured to transmit a sensor signal from an end effector supported by the wrist assembly.

17. The wrist assembly of claim 12, further comprising a link coupling the proximal segment of the first joint to the distal segment of the first joint.

18. The wrist assembly of claim 12, wherein the second joint includes a proximal segment defining a proximal arcuate surface and a distal segment defining a distal arcuate surface.

19. The wrist assembly of claim 18, wherein the electrical cable is positioned relative to the proximal arcuate surface of the second joint and the distal arcuate surface of the second joint such that, during articulation of the wrist assembly, the electrical cable rolls off of the distal arcuate surface of the second joint as the electrical cable rolls on to the proximal arcuate surface of the second joint, and the electrical cable rolls off of the proximal arcuate surface of the second joint as the electrical cable rolls on to the distal arcuate surface of the second joint.

20. The wrist assembly of claim 12, further comprising a second electrical cable, wherein the proximal segment of the first joint defines a second proximal arcuate surface, the distal segment of the first joint defines a second distal arcuate surface, and the second electrical cable is positioned such that, during articulation of the wrist assembly, the second electrical cable rolls off of the second distal arcuate surface as the electrical cable rolls on to the second proximal arcuate surface, and the second electrical cable rolls off of the second proximal arcuate surface as the second electrical cable rolls on to the second distal arcuate surface.

* * * * *